United States Patent [19]

Kamano et al.

[11] 4,113,680

[45] Sep. 12, 1978

[54] METHOD FOR PREPARING 17 α-ESTER-21-HALO PREGNANES

[75] Inventors: Yoshiaki Kamano, Tokyo; Kazuhiko Michishita, Saitama; Teruya Seki; Ichiro Tanaka, both of Tokyo, all of Japan

[73] Assignee: Taisho Pharmaceutical Co., Ltd., Tokyo, Japan

[21] Appl. No.: 671,693

[22] Filed: Mar. 29, 1976

[30] Foreign Application Priority Data

Mar. 31, 1975 [JP] Japan ................................. 50-38914
May 1, 1975 [JP] Japan ................................. 50-52085

[51] Int. Cl.$^2$ ............................................... C07J 5/00
[52] U.S. Cl. ........................ 260/397.45; 260/239.55 R
[58] Field of Search ................. 260/397.45, 239.55 D

[56] References Cited

U.S. PATENT DOCUMENTS

| 3,826,366 | 8/1974 | Cimarusti | 260/239.55 D |
| 3,992,422 | 11/1976 | Green | 260/239.55 D |

*Primary Examiner*—Elbert L. Roberts
*Attorney, Agent, or Firm*—Wenderoth, Lind & Ponack

[57] ABSTRACT

One-step method for preparing 17 α-ester-21-halo pregnanes by reacting 17 α, 21-cyclic orthoesters of 17 α, 21-dihydroxy pregnanes with a halo compound in the presence of an organic polar solvent, simultaneously resulting in halogenation at 21-position and esterification at 17 α-position of said 17 α, 21-cyclic orthoesters, the reaction proceeding in a short period of time without, or substantially without, any unfavorable side-reactions.

15 Claims, No Drawings

METHOD FOR PREPARING 17 α-ESTER-21-HALO PREGNANES

BACKGROUND OF THE INVENTION

Several methods for preparing 17α-ester-21-halo pregnanes have previously been attempted. For example, (a) 17α,21-Dihydroxy pregnane is reacted with methanesulfonyl halide to obtain 17α-hydroxy-21-methanesulfonyloxy pregnane, which is then esterified, and the resultant 17α-ester-21-methanesulfonyloxy pregnane is reacted with lithium halide to give the objective compound. (Japanese Patent Application Publication No. 47-43943)

(b) 17α,21-Cyclic orthoester of 17α,21-dihydroxy pregnane is hydrolyzed to obtain 17α-ester-21-hydroxy pregnane, which is then reacted with methanesulfonyl halide, and the resultant 17α-ester-21-methanesulfonyloxy pregnane is halogenated with lithium halide to give the objective compound. (Deutsche Offenlegungsschrift No. 2432408).

(c) 17α,21-Cyclic orthoester of 17α,21-dihydroxy pregnane is reacted with triphenylmethyl halide in the presence of dichloromethane to give the objective compound. (Deutsche Offenlegungsschrift No. 2432408)

The process (a) consists of several lengthy and complicated steps, and is accompanied by industrial drawbacks such as high cost, low yield and low purity. Especially, when the 17α-hydroxy-21-methanesulfonyloxy pregnane has another hydroxy group, in addition to the 17α-hydroxy group, the esterification of the 17α-hydroxy group should be carried out after the protection of the other hydroxy group. As a result, a further step is required for releasing the protective group after esterification of the 17α-hydroxy group.

The process (b) also has similar disadvantages. Particularly, the last step of halogenation requires heating at a high temperature for a considerable number of hours.

The method (c) enabled simplification of the reaction; however, fission of the cyclic orthoester produces a considerable amount of 21-hydroxy-17α-monoester and 21-monoester-17α-hydroxy pregnanes as by-products. Consequently, the process requires further isolation and purification procedures, resulting in a substantial decrease in yield of the objective compound.

The present inventors have established a novel and industrially excellent process whereby, according to the present invention, the objective 17α-ester-21-halo pregnane can be obtained very easily at high yield as pure crystals by a one-step treatment of 17α,21-cyclic orthoester of 17α,21-dihydroxy pregnane with a halo compound in the presence of an organic solvent, in a very short time at room temperature (about 20° C) or elevated temperature, e.g. up to reflux temperature.

BRIEF SUMMARY OF INVENTION

This invention relates to a new method for preparing pregnanes. More particularly, this invention concerns a method for preparing a 17α-ester-21-halo pregnane having at the 17, 20 and 21 positions the structure

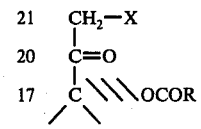

wherein R is selected from the group consisting of alkyl containing 1 to 9 carbon atoms, preferably lower alkyl, cycloalkyl containing 4 to 6 carbon atoms and phenyl, and X is halogen, which comprises reacting a 17α,21-cyclic orthoester of a 17α,21-dihydroxy pregnane having at the 17, 20 and 21 positions the structure

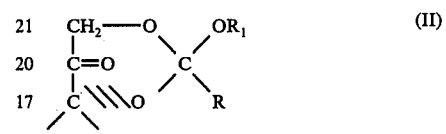

wherein $R_1$ is lower alkyl and R is as defined above, with a halo compound selected from the group consisting of silyl halides, acyl halides, phosphorus oxyhalides, sulfonyl halides, N-haloimides, N-haloamides and phosphorus pentahalides in the presence of an organic polar solvent selected from the group consisting of dimethylformamide(DMF), N-methylpyrrolidone, hexamethylphosphoric triamide(HMPA, hexamethylphosphoramide), dimethylsulfoxide(DMSO) and a mixture of the organic polar solvent and an organic non-polar solvent.

An object of this invention is to provide a new method for preparing 17α-ester-21-halo pregnanes.

Another object of this invention is to provide a new and useful method for preparing 17α-ester-21-halo pregnanes, which are useful as anti-inflammatory agents, in an industrially convenient manner.

DETAILED DESCRIPTION OF THE INVENTION

In this specification and claims, unless otherwise noted, the terms "lower alkyl", "lower alkenyl" and "lower alkoxy" refer to said groups containing up to 5 carbon atoms and being optionally straight or branched; the terms "phenyl" and "phenoxy" refer to each group which may have optionally suitable nucleous substituent such as lower alkyl, nitro, halogen and the like; and the term "halogen" means chloro, bromo, iodo and fluoro.

The steroids of formula (I) are the physiologically active substances that possess glucocorticoid and anti-inflammatory activity, e.g., as described in the references above as well as in "The Annual Report of the Kyoritsu College of Pharmacy", Vol. 19, 1975, pages 13-25.

In a preferred procedure of this invention, the compound of formula (II) is dissolved in an organic polar solvent selected from the group consisting of dimethylformamide, N-methylpyrrolidone, hexamethylphosphoric triamide and dimethylsulfoxide, or a mixture of one of these organic polar solvents and an organic non-polar solvent such as benzene, cylcohexane, tetrahydrofurane, dioxane, ether, chloroform, methylene chloride and the like. The resulting solution is added with a halo compound selected from the group consisting of silyl halides, acyl halides, phosphorus oxyhalides, sulfonyl halides, N-haloimides, N-haloamides and phosphorous pentahalides. The reaction mixture thus obtained is refluxed for 5 – 10 minutes or, preferably, is kept standing at room temperature for 0.5 – 3 hours, to carry out the reaction, at atmospheric pressure. The resulting compound of formula (I) may be refined by recrystallization, and further, if necessary, by column chromatography or thin layer chromatography.

The concentration of the compound of formula (II) in the solvent system employed is generally one part by weight of the compound of formula (II) for 10 to 100 parts by weight of solvent. When a mixture of organic polar and non-polar solvents is employed, the polar solvent should, in general, account for at least 50%, preferably 80%, by weight of said mixture.

In general, in carrying out the reaction of the present invention, 1 to 5 moles of the halo compound are reacted with each mole of the compound of formula (II).

The most important characteristic of the method of this invention is the use of said halo compound in the presence of said organic polar solvent. Such condition enables the simultaneous carrying out of two selective reactions, i.e., the halogenation at the 21-position and the esterification at the 17α-position of the cyclic orthoester of formula (II), which reactions are not accompanied by the drawbacks referred to above in connection with the known methods.

Furthermore, even if a cyclic orthoester of formula (II) having hydroxy groups, e.g., the 11-hydroxy compound, is used, the esterification at the 17α-position is accomplished selectively without affecting such hydroxy groups, and therefore there is no need to protect such hydroxy groups prior to the reaction.

In this invention, suitable silyl halides used as the halo compound include compounds represented by the general formula

wherein one to three of $R_2$, $R_3$, $R_4$ and $R_5$ groups are halogen, and the other or others are independently selected from the group consisting of lower alkyl, lower alkenyl, lower alkoxy and phenyl. Said lower alkyl may be optionally substituted by halogen. In the compounds of formula (III), trimethylsilyl halides, triethylsilyl halides, triisopropylsilyl halides, halomethyldimethylsilyl halides, dimethylsilyl dihalides, triphenylsilyl halides, diphenylsilyl dihalides and methylsilyl trihalides are preferable.

Suitable acyl halides used as the halo compound include compounds represented by the general formula $$R_6—COX \qquad (IV)$$

and

wherein $R_6$ is selected from the group consisting of alkyl consisting 1 to 18 carbon atoms, preferably lower alkyl, alkenyl containing 2 to 18 carbon atoms, preferably lower alkenyl, cycloalkyl containing 4 to 10 carbon atoms, haloformyl, lower alkoxycarbonyl, aryl containing 6 to 12 carbon atoms, e.g. phenyl and naphthyl, and unsaturated lactone rings containing two oxygen atoms and 4 to 7 carbon atoms, for example the ring of coumalic acid, X is halogen, $R_7$ is selected from the group consisting of phenylene, vinylene and alkylene containing 1 to 10 carbon atoms, preferably alkylene of 1 to 8 carbon atoms, at least one of $R_8$ and $R_9$ is halogen and, if only one of $R_8$ and $R_9$ is halogen the other is lower alkoxy. Said alkyl refers to unsubstituted alkyl and alkyl which is substituted by halogen, phenyl or phenoxy; said alkenyl refers to unsubstituted alkenyl and alkenyl which is substituted by phenyl; said cycloalkyl refers to the group which contains one to four cycles; and said aryl refers to the group which contains one or two cycles. In the compounds of formulae (IV) and (V), halides of acetic acid, propionic acid, n- or iso-butyric acid, n- or iso-valeric acid, phenoxyacetic acid, benzoic acid, methylbenzoic acid, cyclohexanoic acid, cinnamic acid, crotonic acid, phthalic acid and oxalic acid are preferable.

Suitable phosphorus oxyhalides used as the halo compound include compounds represented by the general formula

wherein one to three of $R_{10}$, $R_{11}$ and $R_{12}$ are halogen, and the others, if any, are independently selected from the group consisting of lower alkyl, lower alkoxy, phenyl and phenoxy. In the compounds of formula (VI), phosphorus oxytrihalides, phenylphosphorus oxydihalides, diphenylphosphorus oxyhalides, ethylphosphorus oxydihalides, diethylphosphorus oxyhalides, diethoxyphosphorus oxyhalides, ethoxyphosphorus oxydihalides, methylphenylphosphorus oxyhalides, methylphenoxyphosphorus oxyhalides and methoxyphenoxyphosphorus oxyhalides are preferable.

Suitable sulfonyl halides ued as the halo compound in this invention include compounds represented by the general formula $$R_{13}—SO_2X \qquad (VII)$$

wherein $R_{13}$ is selected from the group consisting of hydroxy, lower alkyl and phenyl, and X is halogen. In the compounds of formula (VII), sulfonyl halides, mesyl halides, ethanesulfonyl halides, benzenesulfonyl halides and tosyl halides are preferable.

As the N-haloimide used in this invention as the halo compound, there are used, for example, N-halophthalimide and N-halosuccinimide, and as the N-haloamide in this invention, there is used a compound represented by the general formula $$R_{14}—CONHX \qquad (VIII)$$

wherein $R_{14}$ is lower alkyl and X is halogen. In the compounds of formula (VIII), N-halopropionamide, N-haloisobutyramide and N-haloacetamide are preferable.

As the phosphorus pentahalide used in this invention as the halo compound, there is used a compound represented by the general formula $$P X_5 \qquad (IX)$$

wherein X is halogen. In the compounds of (IX), phosphorus pentachloride, phosphorus pentabromide and phosphorus pentafluoride are preferable.

The starting material of formula (II) may be produced by known methods, for example as described in "Tetrahedron Letters", 1961, pages 448–451. For example, 17α,21-dihydroxy pregnane is reacted with an orthoester represented by the formula $$R-C(OR_1)_3 \qquad (X)$$

wherein R and $R_1$ are as defined above, at 60° – 130° C in the presence of a suitable acidic catalyst in an organic solvent to give the compound of formula (II).

As the orthoester of formula (X), use may be made of the ester of ortho acetic acid, ortho propionic acid, ortho butyric acid, ortho isobutyric acid, ortho valeric acid, ortho isovaleric acid, ortho caproic acid, ortho isocaproic acid, ortho enantoic acid, ortho caprylic acid, ortho cyclobutanecarboxylic acid, ortho cyclopentanecarboxylic acid, ortho hexahydrobenzoic acid and the like.

Typical of the preferred pregnanes of formula (II) are compounds represented by the general formula

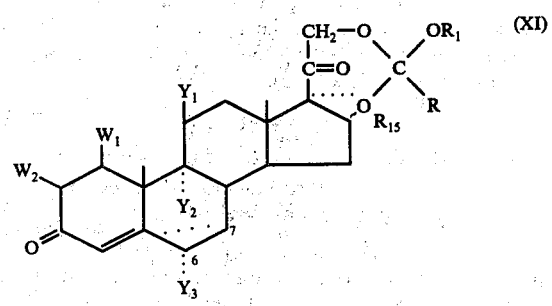

wherein $Y_1$ is halogen or oxo, i.e. ketonic oxygen, $Y_2$ is hydrogen, hydroxy or halogen, or $Y_1$ and $Y_2$, taken together, form an epoxy ring or double bond together with the adjacent carbon atoms, i.e. the carbon atoms to which they are attached, $Y_3$ is halogen, hydrogen or methyl, $W_1$ and $W_2$ are each hydrogen or methyl, or together with the adjacent carbon atoms form a cyclopropane ring or a double bond, $R_{15}$ is methyl, hydrogen, methylene, hydroxy, lower alkoxy or acyloxy containing 2 to 8 carbon atoms, e.g. alkanoyloxy containing 2 to 6 carbon atoms, R and $R_1$ are as defined above, the wavy line (∼) by which $R_{15}$ is attached to the ring indicates the α- or β-configuration, and the dotted line in the ring to which $Y_2$ and $Y_3$ are attached indicates a double or single bond between positions 6 and 7, and corresponding homo-, nor- and enol-forms thereof.

The following working examples provide specific embodiments of the present invention, but are not limitative thereof.

EXAMPLE 1

Preparation of hydrocortisone 17-acetate 21-chloride (17α-acetoxy-21-chloro-4-pregnen-11β-ol-3,20-dione)

To a mixture of 50 mg of hydrocortisone 17,21-methyl orthoacetate (17α,21-(1'-methyl-1'-methoxymethylenedioxy)-4-pregnen-11β-ol-3,20-dione) in 2.5 ml of dimethylformamide (DMF), 0.05 ml of trimethylsilyl chloride was added. The mixture was allowed to stand for 1 hr. at room temperature, and was evaporated in vacuo to give a white solid. This was crystallized from acetone-hexane-isopropylether to give 48 mg of the product, m.p. 253°–254° C.

EXAMPLE 2

Preparation of hydrocortisone 17-propionate 21-chloride (21-chloro-17α-propionyloxy-4-pregnen-11β-ol-3,20-dione)

To a mixture of 200 mg of hydrocortisone 17,21-ethyl orthopropionate (17α,21-(1'-ethyl-1'-ethoxymethylenedioxy)-4-pregnen-11β-ol-3,20-dione) (m.p. 182.5°–183.6° C) in 10 ml of DMF, 0.25 ml of trimethylsilyl chloride was added. The mixture was allowed to stand for 1 hour at room temperature, and then was evaporated in vacuo to give a residue. This was crystallized from acetone to give 189 mg of the product, m.p. 225°–227° C.

EXAMPLE 3

Preparation of hydrocortisone 17-butyrate 21-chloride (17α-butyryloxy-21-chloro-11β-hydroxy-4-pregnen-3,20-dione)

To a solution of 100 mg of hydrocortisone 17,21-methyl orthobutyrate (17α,21 (1'-methoxy-1'-propylmethylenedioxy)-11β-hydroxy-4-pregnen-3,20-dione) in 5 ml of DMF, 0.125 ml of trimethylsilyl chloride was added. The mixture was kept to stand at room temperature for 18 hrs. and was evaporated in vacuo, to yield the crude product. Recrystallization from acetone-hexane afforded 96 mg of the pure product, m.p. 192°–196° C.

EXAMPLE 4

Preparation of hydrocortisone 17-valerate 21-chloride (21-chloro-11β-hydroxy-17α-valeroyloxy-4-pregnen-3,20-dione)

To a solution of 50 mg of hydrocortisone 17,21-methyl orthovalerate (17α,21-(1'-methoxy-1'-butylmethylenedioxy)-11β-hydroxy-4-pregnen-3,20-dione) in 0.25 ml of DMF, 0.06 ml of trimethylsilyl chloride was added. The mixture was allowed to stand at room temperature for 2 hrs., and then evaporated in vacuo. The residue was recrystallized from acetone-hexane to afford 45 mg of the product, m.p. 154°–156° C.

EXAMPLE 5

Preparation of hydrocortisone 17-caproate 21-chloride (17α-caproyloxy-21-chloro-11β-hydroxy-4-pregnen-3,20-dione)

To a mixture of 50 mg of hydrocortisone-17,21-methyl orthocaproate (17α,21-(1'-methoxy-1'-pentylmethylenedioxy)-11β-hydroxy-4-pregnen-3,20-dione) in 0.25 ml of DMF, 0.05 ml of trimethylsilyl chloride was added. The mixture was allowed to stand at room temperature for 0.5 hr. and was evaporated in vacuo to give the crude product. By recrystallization from acetone-hexane-isopropylether, 46 mg of the pure product, m.p. 163°–167° C was obtained.

EXAMPLE 6

Preparation of hydrocortisone 17-benzoate 21-chloride (17α-benzoyloxy-21-chloro-11β-hydroxy-4-pregnen-3,20-dione)

To a mixture of 25 mg of hydrocortisone 17,21-methyl orthobenzoate (17α,21-(1'-methoxy-1'-phenylmethylenedioxy)-11β-hydroxy-4-pregnen-3,20-dione)

(m.p. 208°–210° C) in 0.15 ml of DMF, 0.06 ml of trimethylsilyl chloride was added. After keeping at room temperature for 1 hr., the reaction mixture was evaporated in vacuo to give the crystalline product. Recrystallization of this from acetone-hexane afforded 22.5 mg of the pure product, m.p. 226°–229° C.

EXAMPLE 7

Preparation of hydrocortisone 17-cyclopentanecarboxylate 21-chloride (17α-cyclopentanecarbonyloxy-21-chloro-11β-hydroxy-4-pregnen-3,20-dione)

To a mixture of 25 mg of hydrocortisone 17,21-methyl orthocyclopentane-carboxylate (17α,21-(1'-cyclopentyl-1'-methoxy-methylenedioxy)-11β-hydroxy-4-pregnen-3,20-dione) (m.p. 197°–201° C) in 0.15 ml of DMF, 0.06 ml of trimethylsilyl chloride was added. The reaction mixture was allowed to stand for 2 hrs. at room temperature, then was evaporated in vacuo to give a crude product. The pure one (yield: 22.5 mg m.p. 229°–233° C) was obtained by recrystallization of this from acetone-hexane-isopropylether.

EXAMPLE 8

Preparation of prednisolone 17-acetate 21-chloride (17α-acetoxy-21-chloro-11β-hydroxy-pregna-1,4-diene-3,20-dione)

To a mixture of 50 mg of prednisolone 17,21-methyl orthoacetate (17α,21-(1'-methyl-1'-methoxy-methylenedioxy)-11β-hydroxy-pregna-1,4-diene-3,20-dione) (m.p. 185°–188° C) in 2.5 ml of DMF, 0.05 ml of trimethylsilyl chloride was added. After keeping at room temperature for 1 hr., the reaction mixture was evaporated in vacuo. The residue was recrystallized from acetone to give 46 mg of the pure product, m.p. 254°–255° C.

EXAMPLE 9

Preparation of prednisolone 17-propionate 21-chloride (21-chloro-17α-propionyloxy-11β-hydroxy-pregna-1,4-diene-3,20-dione)

By the similar procedure as described in Example 8, 50 mg of prednisolone 17,21-ethyl orthopropionate (17α,21-(1'-ethyl-1'-ethoxy-methylenedioxy)-11β-hydroxy-pregna-1,4-diene-3,20-dione) (m.p. 225°–227° C) was converted to the product (yield; 45 mg, m.p. 225°–227° C) as indicated in the title.

EXAMPLE 10

Preparation of prednisolone 17-butyrate 21-chloride (21-chloro-17α-butyryloxy-11β-hydroxy-pregna-1,4-diene-3,20-dione)

To a mixture of 50 mg of prednisolone 17,21-methyl orthobutyrate (17α,21-(1'-methoxy-1'-propyl-methylenedioxy)-11β-hydroxy-pregna-1,4-diene-3,20-dione) (m.p. 165°–168° C) in 2.5 ml of DMF, 0.05 ml of trimethylsilyl chloride was added. The reaction mixture was treated by the similar method as described in Example 8. The crude product thus obtained was recrystallized from acetone-hexane to yield 46 mg of the pure product, m.p. 197°–200° C.

EXAMPLE 11

Preparation of prednisolone 17-valerate 21-chloride (21-chloro-17α-valeroyloxy-11β-hydroxy-pregna-1,4-diene-3,20-dione).

To a mixture of 25 mg of prednisolone 17,21-methyl orthovalerate (17α,21-(1'-butyl-1'-methoxy-methylenedioxy)-11β-hydroxy-pregna-1,4-diene-3,20-dione) in 1.25 ml of DMF, 0.03 ml of trimethylsilyl chloride was added. The mixture was allowed to stand at room temperature for 1 hr. By evaporation of the mixture in vacuo, the crude product was obtained. This was recrystallized from acetone-hexane-isopropylether to afford 45.5 mg of the pure product, m.p. 191°–193° C.

EXAMPLE 12

Preparation of prednisolone 17-caproate 21-chloride (17α-caproyloxy-21-chloro-11β-hydroxy-pregna-1,4-dien-3,20-dione)

To a solution of 25 mg of prednisolone 17,21-methyl orthocaproate (17α,21-(1'-methoxy-1'-pentyl-methylenedioxy)-11β-hydroxy-pregna-1,4-diene-3,20dione) in 1.25 ml of DMF, 0.025 ml of trimethylsilyl chloride was added. After keeping at room temperature for 1.8 hrs., the reaction mixture was evaporated in vacuo to give the solid. Recrystallization of this from acetone-hexane-isopropylether gave the pure product (20 mg, m.p. 199°–201° C).

EXAMPLE 13

Preparation of dexamethasone 17-acetate 21-chloride (17α-acetoxy-21-chloro-9α-fluoro-16α-methyl-11β-hydroxy-pregna-1,4-dien-3,20-dione)

To a mixture of 50 mg of dexamethasone 17,21-methyl orthoacetate (9α-fluoro-16α-methyl-17α,21-(1'-methoxy-methylenedioxy)-11β-hydroxy-pregna-1,4-dien-3,20-dione) (m.p. 200°–202° C) in 2.5 ml of DMF, 0.05 ml of trimethylsilyl chloride was added. The mixture was allowed to stand for 2 hrs. at room temperature, and then evaporated in vacuo to give the solid. The pure product (47 mg, m.p. 262.5°–263° C) was obtained by recrystallization of this from acetone-hexane-isopropylether.

EXAMPLE 14

Preparation of dexamethasone 17-propionate 21-chloride (21-chloro-9α-fluoro-16α-methyl-11β-hydroxy-17α-propionyloxy-pregna-1,4-dien-3,20-dione)

To a solution of 238 mg of dexamethasone 17,21-ethyl orthopropionate (9α-fluoro-16α-methyl-17α,21-(1'-ethyl-1'-ethoxy-methylenedioxy)-11β-hydroxy-pregna-1,4-dien-3,20-dione) (m.p. 219°–221° C) in 12 ml of DMF, 0.3 ml of trimethylsilyl chloride was added. After keeping at room temperature for 1.8 hrs., the mixture was evaporated in vacuo. The residue was recrystallized from acetone-hexane to give 215 mg of the pure product, m.p. 240°–243° C.

EXAMPLE 15

Preparation of dexamethasone 17-butyrate 21-chloride (17α-butyryloxy-21-chloro-9α-fluoro-16α-methyl-11β-hydroxy-pregna-1,4-dien-3,20-dione)

To a solution of 30 mg of dexamethasone 17,21-methyl orthobutyrate (9α-fluoro-16α-methyl-17α,21-(1'-methoxy-1'-propyl-methylenedioxy)-11β-hydroxypregna-1,4-dien-3,20-dione) m.p. 166°–169° C) in 1.5 ml of DMF, 0.03 ml of trimethylsilyl chloride was added. After keeping at room temperature for 1.5 hrs., the reaction mixture was evaporated in vacuo. Recrystallization of the residue thus obtained from acetone-hexane afforded 27 mg of the pure product, m.p. 230°–232° C.

EXAMPLE 16

Preparation of dexamethasone 17-valerate 21-chloride (21-chloro-9α-fluoro-16α-methyl-11β-hydroxy-17α-valeroyloxy-pregna-1,4-diene-3,20-dione)

By the similar procedure as described in Example 15, 20 mg of dexamethasone 17,21-methyl orthovalerate (9α-fluoro-16α-methyl-17,21-(1'-butyl-1'-methoxymethylenedioxy)-11β-hydroxy-pregna-1,4-dien-3,20-dione) (m.p. 157°–161° C) was converted to the desired product (yield 17.8 mg., m.p. 193°–195° C).

EXAMPLE 17

Preparation bethamethasone 17-propionate 21-chloride (21-chloro-9α-fluoro-16β-methyl-11β-hydroxy-17α-propionyloxy-pregna-1,4-dien-3,20-dione)

To a solution of 100 mg of betamethasone 17,21-ethyl orthopropionate (9α-fluoro-16β-methyl-17α,21-(1'-ethoxy-1'-ethyl-methylenedioxy)-11β-hydroxy-pregna-1,4-dien 3,20-dione) (m.p. 208°–211° C) in 5 ml of DMF, 0.1 ml of trimethylsilyl chloride was added. The reaction mixture was evaporated in vacuo to give the solid. By recrystallization of this from acetone-hexane, the pure product (92 mg), m.p. 193°–196° C, was obtained.

EXAMPLE 18

Preparation of betamethasone 17-acetate 21-chloride (17α-acetoxy-21-chloro-9α-fluoro-11β-hydroxy-16β-methyl-pregna-1,4-dien-3,20-dione)

By the similar the procedure as described in Example 17, 50 mg of betamethasone 17,21-methyl orthoacetate (9α-fluoro-16β-methyl-17α,21-(1'-methyl-1'-methoxymethylenedioxy)-11β-hydroxy-pregna-1,4-diene-3,20-dione) (m.p. 156°–157° C) was converted to the desired product (yield 47 mg) m.p. 226°–230° C.

EXAMPLE 19

Preparation of betamethasone 17-butyrate 21-chloride (17α-butyryloxy-21-chloro-9α-fluoro-16β-methyl-11β-hydroxy-pregna-1,4-dien-3,20-dione)

By the similar procedure as described in Example 17, the desired product (m.p. 171°–173° C) was obtained from 50 mg of bethamethasone 17,21-methyl orthobutyrate (9α-fluoro-16β-methyl-17α,21-(1'-methoxy-1'-propyl-methylenedioxy)-11β-hydroxy-pregna-1,4-dien-3,20-dione) in the 46 mg yield.

EXAMPLE 20

Preparation of betamethasone 17-isobutyrate 21-chloride (21-chloro-9α-fluoro-17α-isobutyryloxy-11β-hydroxy-16β-methyl-pregna-1,4-dien-3,20-dione)

By the similar procedure as described in Example 17, 30 mg of betamethasone 17,21-methyl orthoisobutyrate (9α-fluoro-11β-hydroxy-17α,21-(1'-isopropyl-1'-methoxy-methylenedioxy)-16β-methyl-pregna-1,4-dien-3,20-dione) (m.p. 173° C) was converted to 27 mg of the desired product, m.p. 192°–194° C.

EXAMPLE 21

Preparation of betamethasone 17-valerate 21-chloride (21-chloro-9α-fluoro-16β-methyl-11β-hydroxy-17α-valeroyloxy-pregna-1,4-dien-3,20-dione)

By the similar procedure as described in Example 17, from 25 mg of betamethasone 17,21-methyl orthovalerate (9α-fluoro-17α,21-(1'-butyl-1'-methoxymethylenedioxy)-11β-hydroxy-16β-methyl-pregna-1,4-dien-3,20-dione), the crude product was obtained. Recrystallization of this from acetone-hexane-isopropylether gave 22 mg of the pure product, m.p. 197°–201° C.

EXAMPLE 22

Preparation of betamethasone 17-isovalerate 21-chloride (21-chloro-9α-fluoro-11β-hydroxy-17α-isovaleroyloxy-16β-methyl-pregna-1,4-dien-3,20-dione)

By the similar method as described in Example 21, 50 mg of betamethasone 17,21-methyl orthoisovalerate (9α-fluoro-11β-hydroxy-17α,21-(1'-isobutyl-1'-methoxy-methylenedioxy)-16β-methyl-pregna-1,4-dien-3,20-dione) (m.p. 175°–176° C) was converted into the desired product (m.p. 231°–233° C; yield, 45 mg).

EXAMPLE 23

Preparation of betamethasone 17-caproate 21-chloride (17α-caproyloxy-21-chloro-9α-fluoro-11β-hydroxy-16β-methyl-pregna-1,4-dien-3,20-dione)

To a mixture of 40 mg of betamethasone 17,21-methyl orthocaproate (9α-fluoro-11β-hydroxy-16β-methyl-17α,21-(1'-pentyl-1'-methoxy-methylenedioxy)-pregna-1,4-dien-3,20-dione) (m.p. 148°–151° C) in 2.5 ml of DMF, 0.05 ml of trimethylsilyl chloride was added. The mixture was allowed to stand at room temperature for 1.5 hrs., and then was evaporated in vacuo to give the solid. By recrystallization from acetone-ether, the pure product, m.p. 175°–177° C was obtained in the 36 mg yield.

EXAMPLE 24

Preparation of betamethasone 17-cyclopentanecarboxylate 21-chloride (21-chloro-17α-cyclopentanecarbonyloxy-9α-fluoro-11β-hydroxy-16β-methyl-pregna-1,4-dien-3,20-dione)

20 mg of betamethasone 17,21-methyl orthocyclopentanecarboxylate (17α,21-(1'-cyclopentyl-1'-methoxy-methylenedioxy)-9α-fluoro-11β-hydroxy-16β-methyl-pregna-1,4-dien-3,20-dione) in 1.2 ml of DMF was converted to the desired product (17 mg), m.p. 229°–231° C, by the similar method as described in Example 23.

EXAMPLE 25

Preparation of betamethasone 17-benzoate-21-chloride (17α-benzoyloxy-21-chloro-9α-fluoro-11β-hydroxy-16β-methyl-pregna-1,4-dien-3,20-dione)

By the similar method as described in Example 21, 50 mg of betamethasone 17,21-methyl orthobenzoate (9α-fluoro-11β-hydroxy-16β-methyl-17α,21-(1'-methoxy-1'-phenyl-methylenedioxy)-pregna-1,4-dien-3,20-dione) was converted to the title compound (yield, 44 mg; m.p. 233+–237° C).

EXAMPLE 26

Preparation of
17α-acetoxy-21-chloro-4-pregnen-3,20-dione

To a mixture of 20 mg of 17α,21-(1'-methyl-1'-methoxy-methylenedioxy)-4-pregnen-3,20-dione (m.p. 175°–177° C) in 1 ml of DMF-methylenechloride (2:1), 0.02 ml of diethoxysilyl dichloride was added. The mixture was allowed to stand at room temperature for 22 hrs., and then was evaporated in vacuo to give the residue. The preparative thin-layer chromatographic separation and recrystallization from acetone provided 14 mg of the title compound (m.p. 219°–221° C).

EXAMPLE 27

Preparation of
17α-acetoxy-21-chloro-9α,11β-oxido-4-pregnen-3,20-dione

To a mixture of 20 mg of 17α,21-(1'-methyl-1'-methoxy-methylenedioxy)-9β,11β-oxido-4-pregnen-3,20-dione in 1 ml of dimethylsulfoxide-methylenechloride (1:1), 0.025 ml of trimethylsilyl chloride was added. The mixture was treated in the similar manner as described in Example 26 to give 13 mg of the pure product (m.p. 195°–199° C) from acetone-hexane.

EXAMPLE 28

Preparation of
17α-benzoyloxy-21-chloro-9α,11β-oxido-16β-methyl-pregna-1,4-dien-3,20-dione To a mixture of 50 mg of 17α,21-(1'-methoxy-1'-phenyl-methylenedioxy)-16β-methyl-9β,11β-oxido-pregna-1,4-dien-3,20-dione (m.p. 148°–150° C) in 25 ml of dimethylsulfoxide, 0.05 ml of trimethylsilyl chloride was added. The mixture was allowed to stand for 1.5 hrs. at room temperature. Then the mixture was evaporated in vacuo to give the solid. This was crystallized from acetone-hexane-isopropylether to yield 42 mg of the pure product, m.p. 145°–149° C.

EXAMPLE 29

Preparation of 6α,9α-difluoro-prednisolone 17-propionate 21-chloride (21-chloro-6α,9α-difluoro-11β-hydroxy-17α-propionyloxy-pregna-1,4-dien-3,20-dione To a solution of 50 mg of 6α,9α-difluoro-17α,21-(1'-ethyl-1'-methoxy-methylenedioxy)-11β-hydroxy-pregna-1,4-dien-3,20-dione (m.p. 187°–189° C) in 1.25 ml of DMF-chloroform (1:1), 0.025 ml of trimethylsilyl chloride was added. After keeping at room temperature for 1.5 hrs., the mixture was evaporated in vacuo to yield the crude product. The pure product (m.p. 227°–229° C) was obtained by recrystallization of this from acetone-ether in the 44 mg yield.

EXAMPLE 30

Preparation of
9α,21-dichloro-11β-hydroxy-16β-methyl-17α-propionyloxy-pregna-1,4-dien-3,20-dione 25 mg of 9α-chloro-17α,21-(1'-ethyl-1'-methoxy-methylenedioxy)-11β-hydroxy-16β-methyl-pregna-1,4-dien-3,20-dione) (m.p. 174°–178° C) was dissolved in 1.5 ml of DMF-dioxane (3:1). The mixture was treated by the similar method as described in Example 26. Recrystallization of the crude product thus obtained from ethyl acetate-hexane afforded 22 mg of the pure product, m.p. 203°–205° C.

EXAMPLE 31

Preparation of
17α-acetoxy-9α,21-dichloro-11β-hydroxy-16β-methyl-pregna-1,4-dien-3,20-dione To a mixture of 25 mg of 9α-chloro-11β-hydroxy-16β-methyl-17,21-(1'-methyl-1'-methoxy-methylenedioxy)-pregna-1,4-dien-3,20-dione (m.p. 165°–168° C) in 1.5 ml of hexamethylphosphoric triamide (HMPA)-CCl₄ (1:5), 0.03 ml of trimethylsilyl chloride was added. The reaction mixture was allowed to stand at room temperature for 18 hrs., and then was evaporated in vacuo. Recrystallization of the solid thus obtained from acetone-hexane gave 22 mg of the pure product (m.p. 218°–235° C(dec.)).

EXAMPLE 32

Preparation of
21-chloro-9α-fluoro-11β-hydroxy-17α-valeroyloxy-4-pregnen-3,20-dione To a mixture of 100 mg of 9α-fluoro-17α,21-(1'-butyl-1'-methoxy-methylenedioxy)-11β-hydroxy-4-pregnen-3,20-dione (m.p. 172°–175° C) in 5 ml of DMF-N-methylpyrrolidone (1:1), 0.1 ml of trimethylsilyl chloride was added. After keeping at room temperature for 1.5 hrs., the mixture was evaporated in vacuo to give the residue. Column chromatographic separation using silicagel and recrystallization from acetone-hexane provided 88 mg of the pure product (m.p. 210°–212° C).

EXAMPLE 33

Preparation of
16α,17α-diacetoxy-21-chloro-9α-fluoro-11β-hydroxy-pregna-1,4-dien-3,20-dione To a mixture of 30 mg of 16α-acetoxy-9α-fluoro-17α,21-(1'-ethoxy-1'-methyl-methylenedioxy)-11β-hydroxy-pregna-1,4-dien-3,20-dione (m.p. 193°–195° C) in 1.7 ml of DMF, 0.03 ml of trimethylsilyl chloride was added. After keeping at room temperature for 1.5 hrs., the reaction mixture was evaporated in vacuo to yield the solid. This was recrystallized from methanol-chloroform to give 27 mg of the pure product, m.p. 297°–299° C.

EXAMPLE 34

Preparation of
17α-acetoxy-21-chloro-9α-fluoro-11β-hydroxy-16α-methoxy-4-pregnen-3,20-dione To a solution of 12 mg of 9α-fluoro-17α,21-(1'-ethoxy-1'-methyl-methylenedioxy)-11β-hydroxy-16α-methoxy-4-pregnen-3,20-dione dissolved in 0.6 ml of HMPA-methylenechloride (2:1), 0.012 ml of trimethylsilyl chloride was added. The mixture was allowed to stand at room temperature for 18 hrs. Then, the mixture was evaporated in vacuo to give crude product. The preparative thin-layer chromatographic separation and recrystallization from acetone-hexane provided 8 mg of the pure product (m.p. 243°–245° C).

EXAMPLE 35

Preparation of 16α-acetoxy-21-chloro-9α-fluoro-11β-hydroxy-17α-propionyloxy-pregna-1,4-dien-3,20-dione The title compound (m.p. 283°–285° C) was obtained by the similar method as described in Example 34 by treatment of 15 mg of 16α-acetoxy-9α-fluoro-17α,21-(1′-ethoxy-1′-ethyl-methylenedioxy)-11β-hydroxy-pregna-1,4-dien-3,20-dione (m.p. 183°–187° C) in 0.5 ml of DMF with 0.015 ml of trimethylsilyl chloride in the 12 mg yield.

EXAMPLE 36

In the procedure of Example 2, when DMF-benzene (1:2) (10 ml) was used as a solvent instead of DMF and the mixture was refluxed for 8 min., the pure product was obtained in the 155 mg yield.

EXAMPLE 37

In the procedure of Example 2, when triethylsilyl chloride was used instead of trimethylsilyl chloride as a reagent, the pure product was obtained in the 192 mg yield.

EXAMPLE 38

In the procedure of Example 2, when 50 mg of the starting material, 2.5 ml of DMF, and as a reagent, 0.8 ml of chloromethyldimethylsilyl chloride instead of trimethylsilyl chloride were used, the desired product was obtained in the 43 mg yield.

EXAMPLE 39

In the procedure of Example 2, a solution of 50 mg of starting material in 3 ml of DMF was cooled at 10° C, and to which, 0.06 ml of dimethylsilyl dichloride was added. After keeping at 10° C for 80 min., the mixture was poured into ice-water. Then, this was extracted with chloroform. The extract was washed with water, dried over $Na_2SO_4$, and evaporated in vacuo to give the crystalline residue. This was recrystallized from acetone to yield 38 mg of the pure product.

EXAMPLE 40

In the procedure of Example 2, a solution of 50 mg of the starting material in 3 ml of DMF-CHCl$_3$(1:1) was cooled at 5°–10° C for 70 min., then mixture was poured into ice-water. This was extracted with chloroform. The extract was washed with water, dried over $Na_2SO_4$, and evaporated in vacuo to give the crude product. This was recrystallized from acetone to give 32 mg of the pure product.

EXAMPLE 41

In the procedure of Example 3, to a solution of 100 mg of the starting material in 5 ml of DMF-dimethylsulfoxide (1:1), 0.13 ml of bromomethyldimethylsilyl chloride was added. After keeping at room temperature for 3 hrs., the mixture was evaporated in vacuo to give the crude product. Recrystallization of this from acetone-hexane gave 90 mg of the pure product.

EXAMPLE 42

In the procedure of Example 3, a solution of 50 mg of the starting material in 2.5 ml of DMF-chloroform (1:1) was cooled at 10° C, 0.06 ml of diphenylsilyl dichloride was added. After keeping at 10° C for 3 hrs., the reaction mixture was poured into ice-water. Then, this was extracted with chloroform. The extract was washed with water, dried over $Na_2SO_4$, and evaporated in vacuo to give the crude product. The pure one was obtained by recrystallization of this from acetone-hexane in the 42 mg yield.

EXAMPLE 43

In the procedure of Example 9, when triisopropylsilyl chloride was used instead of trimethylsilyl chloride as a solvent, the desired product was obtained in the 44 mg yield.

EXAMPLE 44

In the procedure of Example 9, when triethylsilyl chloride was used instead of trimethylsilyl chloride as a reagent, the desired product was obtained in the 42 mg yield.

EXAMPLE 45

In the procedure of Example 11, when dimethylvinylsilyl chloride was used instead of trimethylsilyl chloride as a reagent, 21 mg of the pure compound was obtained.

EXAMPLE 46

In the procedure of Example 14, a mixture of 60 mg of the starting material, 3.0 ml of DMF, and 0.08 ml of triethylsilyl chloride was allowed to stand at room temperature for 110 min. After treatment of the reaction mixture by the similar method as described in Example 14, the pure product was obtained, in the 55 mg yield.

EXAMPLE 47

In the procedure of Example 14, 202 mg of product was obtained, when triisopropylsilyl chloride was used instead of trimethylsilyl chloride as a reagent.

EXAMPLE 48

In the procedure of Example 14, a mixture prepared from 30 mg of the starting material, 1.0 ml of dimethylsulfoxide, and 0.05 ml of dimethylsilyl dichloride was allowed to stand at 8°–10° C for 100 min. The mixture was poured into ice-water and extracted with chloroform. The extract was washed with water, dried over $Na_2SO_4$ and evaporated in vacuo to give the residue. The pure product was obtained by recrystallization from acetone-hexane in the 25 mg yield.

EXAMPLE 49

In the procedure of Example 15, 26 mg of product was obtained, when triethylsilyl chloride was used instead of trimethylsilyl chloride as a reagent.

EXAMPLE 50

In the procedure of Example 15, 24 mg of the product was obtained, when dimethylvinylsilyl chloride was used instead of trimethylsilyl chloride as a reagent.

EXAMPLE 51

In the procedure of Example 17, when triisopropylsilyl chloride was used as a reagent instead of trimethylsilyl chloride, 91 mg of pure product was obtained.

EXAMPLE 52

In the procedure of Example 17, 93 mg of the product was obtained, when triethylsilyl chloride was used as a reagent instead of trimethylsilyl chloride.

EXAMPLE 53

In the procedure of Example 19, 42 mg of desired compounds was obtained, when DMF-dimethylsulfoxide (1:1) and triisopropylsilyl chloride were used instead of DMF and trimethylsilyl chloride, respectively.

EXAMPLE 54

In the procedure of Example 21, when diethylsilyl dichloride was used as a reagent instead of trimethylsilyl chloride, 21 mg of the product was obtained.

EXAMPLE 55

Preparation of betamethasone 17-acetate 21-bromide (17α-acetoxy-21-bromo-9α-fluoro-11β-hydroxy-16β-methyl-pregna-1,4-dien-3,20-dione)

To a mixture of 25 mg of betamethasone 17,21-methyl orthoacetate (m.p. 156°–157° C) in 0.7 ml of DMF, 0.08 ml of trimethylsilyl bromide was added. After keeping at room temperature for 100 min., the mixture was poured into ice-water and extracted with chloroform. The extract was washed with aq. sodium bicarbonate solution and water, dried over $Na_2SO_4$ and evaporated in vacuo to give the crude product. The pure product (m.p. 209°–212° C) was obtained by recrystallization from ethyl acetate-hexane in the 22 mg yield.

EXAMPLE 56

Preparation of betamethasone 17-propionate 21-bromide (21-bromo-9α-fluoro-11β-hydroxy-16β-methyl-17β-propionyloxy-pregna-1,4-dien-3,20-dione)

(a) A mixture from 50 mg of betamethasone 17,21-ethyl orthopropionate (m.p. 208°–211° C), 1.5 ml of DMF and 0.15 ml of trimethylsilyl bromide was allowed to stand at room temperature for 2 hrs., then, treatment of the mixture by the similar method as described in Example 55 provided the crude product. The pure product (m.p 203°–205° C) was obtained by recrystallization from acetone-hexane in the 44 mg yield.

(b) In the procedure (a) as described above, when 25 mg of the starting material dissolved in 1 ml of DMF-dimethylsulfoxide-chloroform (2:2:1) was treated with 0.08 ml of triphenylsilyl bromide, the pure product as obtained in the 21 mg yield.

EXAMPLE 57

Preparation of betamethoasone 17-butyrate 21-bromide (21bromo-17α-butyryloxy-9α-fluoro-11β-hydroxy-16β-methyl-pregna-1,4-dien-3,20-dione)

When a solution of 25 of betamethasone 17,21 -methyl orthobutyrate (m.p. 148° C) dissolved in 0.9 ml of DMF was treated by the similar method as described in Example 55, the crude product was obtained. Recrystallization of this from ethyl acetate-hexane gave 21 mg of the pure product, m.p. 183°–185° C.

EXAMPLE 58

Preparation of dexamethasone 17-propionate 21-bromide (21-bromo-9α-fluoro-11β-hydroxy-16α-methyl-17α-propionyloxy-pregna-1,4-dien-3,20-dione)

(a) A mixture prepared from 25 mg of dexamethasone 17,21-ethyl orthopropionate (m.p. 180°–184° C), 0.9 ml of DMF and 0.08 ml of trimethylsilyl bromide was treated by the similar method as described in Example 55. 23 mg of the pure product (m.p. 224°–226° C) was obtained by recrystallization of the crude product.

(b) In the procedure (a), when triphenylsilyl bromide instead of trimethylsilyl bromide was used as a reagent, and the crude product thus obtained was purified by the preparative thin-layer chromatography, the desired product (m.p. 223°–226° C (dec.)) was obtained in the 20 mg yield.

EXAMPLE 59

Preparation of dexamethasone 17-butyrate 21-bromide (21-bromo-17α-butyryloxy-9α-fluoro-11β-hydroxy-16α-methyl-pregna-1,4-dien-3,20-dione)

A mixture prepared from 25 mg of dexamethasone 17,21-methyl orthobutyrate (m.p. 166°–169° C), 1 ml of DMF and 0.08 ml of trimethylsilyl bromide was treated by the similar method as described in Example 55. Recrystallization of the crude product thus obtained from acetone-hexane provided 21 mg of the pure product, m.p. 221°–224° C (dec.).

EXAMPLE 60

Preparation of betamethasone 17-propionate 21-iodide (9α-fluoro-11β-hydroxy-21-iodo-16β-methyl-17α-propionyloxy-pregna-1,4-dien-3,20-dione)

To a solution of 25 mg of betamethasone 17,21-ethyl orthopropionate (m.p. 208°–211° C) in 1 ml of DMF, 0.08 ml of trimethylsilyl iodide was added. After keeping at room temperature for 120 min., the reaction mixture was poured into ice-water and extracted with chloroform. The extract was washed with aq. sodium bicarbonate solution and water, dried over $Na_2SO_4$ and evaporated in vacuo to give the crude product. The pure product was obtained by recrystallization from ethyl acetate-hexane in the 21 mg yield (m.p. 167°–169° C (dec.)).

EXAMPLE 61

Preparation of betamethasone 17-butyrate 21-iodide (17α-butyryloxy-9α-fluoro-11β-hydroxy-21iodo-16β-methyl-pregna-1,4-diene-3,20-dione)

To a solution of 25 mg of betamethasone 17,21-methyl orthobutyrate (m.p. 148° C) dissolved in 1 ml of DMF, 0.08 ml of trimethylsilyl iodide was added. After treatment of the reaction mixture by similar method as described in Example 60, the pure product (m.p. 161°–163° C) was obtained in the 22 mg yield.

EXAMPLE 62

Preparation of dexamethasone 17-propionate-21-iodide (9α-fluoro-11β-hydroxy-21-iodo-16α-methyl-17α-propionyloxy-pregna-1,4-dien-3,20-dione)

A mixture prepared from 25 mg of dexamethasone 17,21-ethyl orthopropionate (m.p. 219°–221° C), 1 ml of DMF and 0.08 ml of trimethylsilyl iodide was treated by the similar method as described in Example 60. Recrystallization of the crude product from acetone-hexane provided 23 mg of the pure product, m.p. 222°–223° C (dec.).

EXAMPLE 63

Preparation of betamethasone 17-propionate 21-fluoride(9α,21-difluoro11β-hydroxy-16β-methyl-17α-propionyloxy-pregna-1,4-dien-3,20-dione)

To a solution of 25 mg betamethasone 17,21-ethyl orthopropionate (m.p. 208°–211° C) in 1 ml of DMF, 0.1 ml of trimethylsilyl fluoride was added. After keeping at room temperature for 2 hrs., the mixture was poured into ice-water, dried over $Na_2SO_4$ and evaporated in vacuo to give the crude product. This was recrystallized from acetone-hexane to afford 21 mg of the pure product, m.p. 221°–224° C.

EXAMPLE 64

Preparation of betamethasone 17-butyrate 21-fluoride (17α-butyryloxy-9α,21-difluoro-11β-hydroxy-16β-methyl-pregna-1,4-dien-3,20-dione)

To a solution of 25 mg of betamethasone 17,21-methyl orthobutyrate (m.p. 148° C) in 1 ml of DMF, 0.1 ml of trimethylsilyl fluoride was added. When the mixture was reacted in the similar manner as described in Example 63, the pure product (m.p. 246°–248° C) was obtained in the 20 mg yield.

EXAMPLE 65

Preparation of betamethasone 17-acetate,21-fluoride (17α-acetoxy-9α,21-difluoro-11β-hydroxy-16β-methyl-pregna-1,4-dien-3,20-dione)

When a mixture prepared from 25 mg of betamethasone 17,21-ethyl orthoacetate (m.p. 156°–157° C), 1.0 ml of DMF and 0.1 ml of trimethylsilyl fluoride was treated by the similar method as described in Example 63, the pure product (m.p. 248°–251° C) was obtained by recrystallization from ethyl acetate-hexane in the 22 mg yield.

EXAMPLE 66

Preparation of dexamethasone 17-propionate 21-fluoride (9α,21-difluoro-11β-hydroxy-16α-methyl-17α-propionyloxy-pregna-1,4-dien-3,20-dione)

When a mixture prepared from 25 mg of dexamethasone 17,21-ethyl orthopropionate (m.p. 219°–221° C), 1 ml of DMF and 0.1 ml of trimethylsilyl fluoride was treated by the similar method as described in Example 63, the crude product was obtained. Recrystallization from acetone-hexane gave 21 mg of the pure product (m.p. 218°–222° C).

EXAMPLE 67

Preparation of hydrocortisone 17-acetate 21-chloride (17α-acetoxy-21-chloro-4-pregnene-11β-ol-3,20-dione)

To a solution of hydrocortisone 17,21-methyl orthoacetate (17α,21-(1'-methoxy-1'-methyl-methylenedioxy)-4-pregnene-11β-ol-3,20-dione) (300 mg, m.p. 222°–224° C) dissolved in dimethylformamide (abbreviate DMF below) (5 mg), acetyl chloride (0.5 ml) was added. The reaction mixture was allowed to stand at room temperature for 1 hr. After the reaction mixture was concentrated in vacuo, a mixture of acetone-hexane-isopropyl ether was added to the residue. The crude crystals thus obtained were recrystallized from the same solvent. Yield 275 mg, m.p. 253°–254° C.

EXAMPLE 68

Preparation of hydrocortisone 17-propionate 21-chloride (21-chloro-17α-propionyloxy-4-pregnene-11β-ol-3,20-dione)

To a solution of hydrocortisone 17,21-ethyl orthopropionate (17α,21-(1'-ethoxy-1'-ethyl-methylenedioxy)-4-pregnene-11β-ol-3,20-dione) (120 mg, m.p. 182.5°–183.5° C) dissolved in DMF (2 ml), propionyl chloride (0.2 ml) was added. The reaction mixture was allowed to stand at room temperature for 1 hr. The reaction mixture was then concentrated in vacuo to give the crude product, which was recrystallized from acetone-hexane. Yield 113 mg, m.p. 225°–227° C.

EXAMPLE 69

Preparation of hydrocortisone 17-butyrate 21-chloride (17α-butyryloxy-21-chloro-4-pregnene-11β-ol-3,20-dione)

To a solution of hydrocortisone 17,21-methyl orthobutyrate (17α,21-(1'-methoxy-1'-propyl-methylenedioxy)-4-pregnene-11β-ol-3,20-dione) (140 mg, m.p. 185.5°–187.5° C) dissolved in DMF (2.5 ml), acetyl chloride (0.25 ml) was added. The reaction mixture was allowed to stand at room temperature for 1 hr. The reaction mixture was then concentrated in vacuo to give the crude product, which was recrystallized from acetone-hexane. Yield 140 mg, m.p. 193°–196° C.

EXAMPLE 70

Preparation of hydrocortisone 17-valerate 21-chloride (17α-valeryloxy-21-chloro-4-pregnene-11β-ol-3,20-dione)

To a solution of hydrocortisone 17,21-methyl orthovalerate (17α,21-(1'-methoxy-1'-butyl-methylenedioxy)-4-pregnene-11β-ol-3,20-dione) (60 mg, m.p. 163°–165° C) dissolved in DMF (1 ml), isobutyryl chloride (0.1 ml) was added. The reaction mixture was allowed to stand at room temperature for 50 min. and then evaporated in vacuo to give the crude product, which was recrystallized from acetone-hexane-isopropyl ether. Yield 55 mg, m.p. 154°–156° C.

EXAMPLE 71

Preparation of hydrocortisone 17-caproate 21-chloride (17α-caproyloxy-21-chloro-4-pregnene-11β-ol-3,20-dione)

To a solution of hydrocortisone 17,21-methyl orthocaproate (17α,21-(1'-methoxy-1'-pentyl-methylenedioxy)-4-pregnene-11β-ol-3,20-dione) (90 mg, m.p. 119°–120° C) dissolved in DMF (1.5 ml), caproyl chloride (0.15 ml) was added. The reaction mixture was allowed to stand at room temperature for 1 hr. and then evaporated in vacuo to give the crude product, which was recrystallized from acetone-hexane-isopropyl ether. Yield 82 mg, m.p. 163°–167° C.

EXAMPLE 72

Preparation of hydrocortisone 17-benzoate 21-chloride (17α-benzoyloxy-21-chloro-4-pregnene-11α-ol-3,20-dione)

To a solution of hydrocortisone 17,21-methyl orthobenzoate (17α,21-(1'-methoxy-1'-phenyl-methylenedioxy)-4-pregnene-11β-ol-3,20-dione) (60 mg, m.p. 208°–210° C) dissolved in DMF(1.2 ml), acetyl chloride(0.1 ml) was added. The reaction mixture was allowed to stand at room temperature for 70 min., and then evaporated in vacuo to give the product, which was recrystallized from acetone-hexane. Yield 54.5 mg, m.p. 226°–228° C.

EXAMPLE 73

Preparation of hydrocortisone 17-cyclopentanecarboxylate 21-chloride (17α-cyclopentanecarbonyloxy-21-chloro-4-pregnene-11β-ol-3,20-dione)

To a solution of hydrocortisone 17,21-methyl orthocyclopentanecarboxylate (17α,21-(1'-cyclopentyl-1'-methoxy-methylenedioxy)-4-pregnene-11β-ol-3,20-dione) (90 mg, m.p. 197°–201° C) dissolved in DMF(1.8 ml), caproyl chloride (0.15 ml) was added. The reaction mixture was allowed to stand at room temperature for 70 min. The solvent was then evaporated in vacuo to give the crude product, which was recrystallized from acetone-hexane-isopropyl ether. Yield 80 mg, m.p. 230°–233° C.

EXAMPLE 74

In an analogous experiment of Example 68, when benzoyl chloride and DMF-dimethyl sulfoxide (1:1) were used instead of propionyl chloride and DMF, respectively, the pure product was obtained in the 112 mg yield after keeping of the reaction mixture at room temperature for 80 min. by the similar method as described in Example 68.

EXAMPLE 75

In an analogous experiment of Example 68, when acetyl chloride and dimethyl sulfoxide were used instead of propionyl chloride and DMF, respectively, the pure product was obtained in the 114 mg yield after keeping of the reaction mixture at room temperature for 60 min. by the similar method as described in Example 68.

EXAMPLE 76

An analogous experiment of Example 68 by using phenoxyacetyl chloride instead of propionyl chloride provided 112 mg of the pure product after the similar treatment.

EXAMPLE 77

When the similar procedure as described in Example 68 was carried out by using acetyl chloride and DMF-dichloromethane(1:1) instead of propionyl chloride and DMF, respectively, the pure product was obtained in the 114 mg yield.

EXAMPLE 78

When the similar procedure as described in Example 68 was carried out by using 2-phenoxypropionyl chloride and DMF-N-methylpyrrolidine(1:1) instead of propionyl chloride and DMF, respectively, the pure product was obtained in the 112 mg yield.

EXAMPLE 79

When the similar procedure as described in Example 68 was carried out by using p-methylbenzoyl chloride and hexamethylphosphoramide-chloroform (1:1) instead of propionyl chloride and DMF, respectively, the pure product was obtained in the 112 mg yield.

EXAMPLE 80

An analogous experiment of Example 68 with 60 mg of coumaryl chloride instead of propionyl chloride as reagent and 3 ml of DMF as solvent provided the crude product by the similar treatment. The crude product was recrystallized from acetone-hexane to give 110 mg of the pure product after the preparative thin-layer chromatographic separation.

EXAMPLE 81

An analogous experiment of Example 68 by using phenylacetyl chloride(60 mg) instead of propionyl chloride provided 112 mg of the pure product after the similar treatment.

EXAMPLE 82

In an analogous experiment of Example 68, when bromoacetyl chloride(45 mg) and DMF-hexamethylphosphoramide-carbon tetrachloride (2:2:1) (1.5 ml) were used instead of propionyl chloride and DMF, respectively, the pure product was obtained from the starting material (60 mg) in the 56 mg yield after the similar treatment.

EXAMPLE 83

In an analogous experiment of Example 68, when cyclohexanecarbonyl chloride(0.1 ml) and DMF-dimethyl sulfoxide-chloroform(2:2:1) (1.5 ml) were used instead of propionyl chloride and DMF, respectively, the pure product was obtained from the starting material (60 mg) in the 57 mg yield after the similar treatment.

EXAMPLE 84

When the similar procedure as described in Example 69 was carried out by using chloroacetyl chloride(0.22 ml) instead of acetyl chloride, the starting material (120 mg) and DMF (2.2 ml), respectively, the pure product was obtained in the 112 mg yield.

EXAMPLE 85

An analogous experiment of Example 84 by using dichloroacetyl chloride (100 mg) instead of acetyl chloride provided 113 mg of the pure product after the similar treatment.

EXAMPLE 86

An analogous experiment of Example 69 by using the starting material (60 mg), crotonyl chloride (48 mg) instead of acetyl chloride as reagent, and dimethyl sulfoxide (0.3 ml) instead of DMF as solvent provided the crude product by the similar treatment. The crude product was recrystallized from acetone-hexane to give 50 mg of the pure product after the preparative thin-layer chromatographic separation.

EXAMPLE 87

An analogous experiment of Example 86 by using cinnamoyl chloride instead of crotonyl chloride provided 51 mg of the pure product after the similar treatment.

EXAMPLE 88

In an analogous procedure of Example 69, to the starting material (90 mg) dissolved in dimethyl sulfoxide-hexamethylphosphoramide-dichloromethane (2:2:1) (2 ml), naphthoyl chloride (10 mg) was added. The reaction mixture was allowed to stand at room temperature for 75 min. Then, after adsorption on thin-layer chromatographic plate (silica gel) directly, the reaction mixture was subjected to preparative thin-layer chromatography. Recrystallization of the crude product from acetone-hexane gave the pure product. Yield 78 mg.

EXAMPLE 89

In an analogous experiment of Example 88, in a solution of the starting material (30 mg) dissolved in N-methylpyrrolidone-dichloromethane (5:1) (1 ml). acetyl chloride (28 mg) was added. The reaction mixture was allowed to stand at room temperature for 55 min. Then the reaction mixture was treated by the similar method as described in Example 87. Yield 27 mg.

EXAMPLE 90

When the similar procedure as described in Example 70 was carried out by using dimethyl sulfoxide (1.2 ml) and pivaloyl chloride instead of DMF and isobutyryl chloride, respectively, the pure product was obtained in the 56 mg yield.

EXAMPLE 91

An analogous experiment of Example 70 by using n-undecanoyl chloride (0.06 ml) instead of isobutyryl chloride, the starting material (30 mg) and DMF (0.6 ml) provided the crude product by the preparative thin-layer chromatographic separation after keeping of the reaction mixture at room temperature for 80 min.

The crude product was then recrystallized from acetone-hexane-isopropyl ether to give 26 mg of the pure product.

EXAMPLE 92

In an analogous experiment of Example 72, to a solution of the starting material (30 mg) dissolved in DMF-dimethyl sulfoxide (1:1) (0.6ml), n-undecanoyl chloride (0.08 ml) was added. The reaction mixture was allowed to stand at room temperature for 90 min. Then the reaction mixture was subjected to preparative thin-layer chromatography to give the crude product which was treated by the similar method as described in Example 72. Yield 26 mg.

EXAMPLE 93

When the similar procedure as described in Example 92 was carried out by using DMF-chloroform (3:1) (0.6 ml) and n-octanoyl chloride (0.07 ml) instead of DMF-dimethyl sulfoxide (1:1) and n-undecanoyl chloride, respectively, the pure product was obtained in the 26.5 mg yield.

EXAMPLE 94

An analogous experiment of Example 93 by using o-methylbenzoyl chloride instead of n-octanoyl chloride provided 24.5 mg of the pure product after the similar treatment.

EXAMPLE 95

Preparation of prednisolone 17-acetate 21-chloride (17α-acetoxy-21-chloropregna-1,4-diene-11β-hydroxy-3,20-dione)

To a solution of prednisolone 17,21-methyl orthoacetate (17α,21-(1'-methoxy-1'-methyl-methylenedioxy)-pregna-1,4-diene-11β-hydroxy-3,20-dione) (60 mg m.p. 185°–188° C) dissolved in DMF (1.2 ml), acetyl chloride (0.12 ml) was added. The reaction mixture was allowed to stand at room temperature for 60 min. The reaction mixture was then concentrated in vacuo to give the crude product, which was recrystallized from acetone. Yield 57 mg.

EXAMPLE 96

Preparation of prednisolone 17-propionate 21-chloride (21-chloro-17α-propionyloxy-pregna-1,4-diene-11β-hydroxy-3,20-dione)

An analogous experiment of Example 95 by using prednisolone 17,21-ethyl orthopropionate (17α,21-(1'-ethoxy-1'-ethyl-methylenedioxy)-pregna-1,4-diene-11β-hydroxy-3,20-dione) (60 mg, m.p. 180°–184° C) provided 5 mg of the pure product after the similar treatment.

EXAMPLE 97

Preparation of prednisolone 17-butyrate 21-chloride (17α-butyryloxy-21-chloro-pregna-1,4-diene-11β-hydroxy-3,20-dione)

To a solution of prednisolone 17,21-methyl orthobutyrate (17α,21-(1'-methoxy-1'-propyl-methylenedioxy)-pregna-1,4-diene-11β-hydroxy-3,20-dione) (60 mg, m.p. 165°–168° C) dissolved in dimethyl sulfoxide (1.2 ml), m-methyl-benzoyl chloride (0.1 ml) was added. The reaction mixture was allowed to stand at room temperature for 60 min. The reaction mixture was then subjected to preparative thin-layer chromatography to give the crude product, which was recrystallized from acetone-hexane. Yield 55 mg. m.p. 198°–200° C.

EXAMPLE 98

Preparation of prednisolone 17-valerate 21-chloride (21-chloro-17α-valeryloxypregna-1,4-dione-11β-hydroxy-3,20-dione)

To a solution of prednisolone 17,21-methyl orthovalerate (17α,21-(1'-butyl-1'-methoxy-methylenedioxy)-pregna-1,4-diene-11β-hydroxy-3,20-dione) (30 mg, m.p. 157°–159° C) dissolved in N-methylpyrrolidone-DMF-carbon tetrachloride (2:2:1) (0.08 ml), m-chlorobenzoyl chloride (30 mg) was added. The reaction mixture was allowed to stand at room temperature for 80 min. The reaction mixture was then subjected to preparative thin-layer chromatography to give the crude product, which was recrystallized from acetone-hexane-isopropyl ether. Yield 25 mg, m.p. 191°–193° C.

EXAMPLE 99

Preparation of prednisolone 17-caproate 21-chloride (17α-caproyloxy-21-chloro-pregna-1,4-diene-11β-hydroxy-3,20-dione)

(a) To a solution of prednisolone 17,21-methyl orthocaproate (17α,21-(1'-methoxy-1'-pentyl-methylenedioxy)-pregna-1,4-diene-11β-hydroxy-3,20-dione) (60 mg, m.p. 137°–141° C) dissolved in hexamethylphosphoramide-dichloromethane (3:1), acetyl chloride (0.1 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate an concentrated in vacuo to give the product, which was recrystallized from acetonehexane-isopropyl ether. Yield 52 mg, m.p. 199°–201° C.

(b) When the similar procedure as described in (a) was carried out by using DMF and valeryl chloride instead of hexamethylphosphoramide-dichloromethane (3:1) and acetyl chloride, respectively, the pure product was obtained in the 54 mg yield.

(c) When the similar procedure as described in (a) was carried out by using DMF and isovaleryl chloride instead of hexamethylphosphoramide-dichloromethane (3:1) and acetyl chloride, respectively, the pure product was obtained in the 53 mg yield.

(d) When the similar procedure as described in (a) was carried out by using DMF and n-tetradecanoyl chloride instead of hexamethylphosphoramide-dichloromethane (3:1) and acetyl chloride, respectively, the pure product was obtained in the 52 mg yield.

(e) In an analogous experiment of (a), to a solution of the starting material (30 mg) dissolved in DMF (0.6 ml), caproyl chloride (0.05 ml) was added. The reaction mixture was allowed to stand at room temperature for 60 min. Then the reaction mixture was adsorbed on silica gel thin-layer chromatographic plate directly. The plate was developed with benzene-acetone mixture. The adsorption zone corresponding to Rf value of the product was collected by the aid of uv-lamp. The compound was extracted with chloroform-methanol (4 : 1) mixture and the extract was concentrated in vacuo. The crude product thus obtained was recrystallized from acetone-hexane-isopropyl ether to give 25 mg of the pure sample.

EXAMPLE 100

In an analogous experiment of Example 95, oxalyl chloride (0.08 ml) was used instead of acetyl chloride. The reaction mixture was allowed to stand at room temperature for 45 min. This was poured into ice-water and extracted with chloroform. The extract was washed with 2% sodium bicarbonate soln. and water, dried over sodium sulfate and concentrated in vacuo to give the crude product, which was recrystallized from acetone. Yield 52 mg.

EXAMPLE 101

An analogous experiment of Example 96 by using phthalyl chloride (5.5 mg) instead of acetyl chloride provided the crude product after keeping of the reaction mixture at room temperature for 45 min. by the similar treatment. The crude product was recrystallized from acetone to give 52 mg of the pure product.

EXAMPLE 102

In an analogous experiment of Example 97, when DMF and sebacyl chloride (5.5 mg) were used instead of dimethyl sulfoxide and m-methylbenzoyl chloride, respectively, the pure preduct was obtained in the 51 mg yield after keeping of the reaction mixture at room temperature for 70 min. by the method as described in Example 97.

EXAMPLE 103

Preparation of dexamethasone 17-acetate 21-chloride
(17α-acetoxy-21-chloro-9α-fluoro-16α-methyl-pregna-1,4-diene-11β-hydroxy-3,20-dione)

(a) To a solution of dexamethasone 17, 21-methyl orthoacetate (9α-fluoro-16α-methyl-17α, 21-(1'-methoxy-1'-methyl-methylenedioxy)-pregna-1,4-diene-11β-hydroxy-3,20-dione) (120 mg, m.p. 200°-202° C) dissolved in DMF (2.4 ml), acetyl chloride (0.24 ml) was added. The reaction mixture was allowed to stand at room temperature for 65 min. The reaction mixture was then poured into ice-water and extracted with chloroform. The extract was washed with 2% sodium bicarbonate soln. and water, dried over sodium sulfate and concentrated in vacuo to give the crude product, which was recrystallized from acetone-hexane-isopropyl ether. Yield 114 mg, m.p. 262°-263° C (decomp.).

(b) When the similar procedure as described in (a) was carried out by using DMF-chloroform (2:1) and m-bromobenzoyl chloride (100 mg) instead of DMF and acetyl chloride, respectively, the pure product was obtained in the 110 mg yield.

(c) An analogous experiment of (a) by using the starting material (30 mg), dimethyl sulfoxide (0.6 ml) instead of DMF as solvent, and fumaryl dichloride (30 mg) instead of acetyl chloride as reagent provided the crude product after the preparative thin-layer chromatographic separation of the reaction mixture directly. The crude product was recrystallized from acetone-hexane-isopropyl ether to give 24 mg of the pure product.

EXAMPLE 104

Preparation of dexamethasone 17-propionate 21-chloride
(21-chloro-9α-fluoro-16α-methyl-17α-propionyloxy-pregna-1,4-diene-11β-hydroxy-3,20-dione)

(a) To a solution of dexamethasone 17,21-ethyl orthopropionate (9α-fluoro-16α-methyl-17α,21-(1'-ethoxy-1'-ethyl-methylenedioxy)-pregna-1,4-diene-11β-hydroxy-3,20-dione) (60 mg, m.p. 219°-221° C) dissolved in DMF (1.2 ml), acetyl chloride (0.1 ml) was added. The reaction mixture was allowed to stand at room temperature for 65 min. The reaction mixture was poured into ice-water and extracted with chloroform. The extract was washed with 2% sodium bicarbonate soln., then thoroughly with water, dried over sodium sulfate and concentrated in vacuo to give the crude product, which was recrystallized from acetone-hexane mixture. Yield 53 mg, m.p. 241°-243° C.

(b) An analogous experiment of (a) by using adipyl chloride (50 mg) instead of acetyl chloride provided 55 mg of the pure product after the similar treatment.

(c) An analogous experiment (a) by using adamantanecarbonyl chloride (60 mg) instead of acetyl chloride provided the crude product by the preparative thin-layer chromatographic separation of the reaction mixture. The crude product was recrystallized from acetone-hexane mixture to give 52 mg of the pure product.

(d) An analogous experiment of (a) by using chloroacetyl chloride instead of acetyl chloride provided 54 mg of the pure product after the similar treatment.

(e) An analogous experiment of (a) by using DMF-chloroform (1 : 1) and benzoyl chloride instead of DMF and acetyl chloride, respectively, provided 52 mg of the pure product after the similar treatment.

(f) An analogous experiment of (a) by using dimethyl sulfoxide and butyryl chloride instead of DMF and acetyl chloride, respectively, provided 53 mg of the pure product after the similar treatment.

(g) An analogous experiment of (a) by using DMF-hexamethylphosphoramidecarbon tetrachloride (3 : 2 : 1) and cyclohexanecarbonyl chloride instead of DMF and acetyl chloride, respectively, provided 52 mg of the pure product after the preparative thin-layer chromatographic separation after the similar treatment.

EXAMPLE 105

Preparation of dexamethasone 17-butyrate 21-chloride (17α-butyryloxy-21-chloro-9α-fluoro-16α-methyl-pregna-1,4-diene-11β-hydroxy-3,20-dione)

(a) To a solution of dexamethasone 17,21-methyl orthobuutyrate (9α-fluoro16α-methyl-17α,21-(1'-methoxy-1'-propyl-methylenedioxy)-pregna-1,4-diene-11β-hydroxy-3,20-dione) (60 mg, m.p. 166°-169° C) dissolved in dimethyl sulfoxide (1.2 ml), acetyl chloride (0.10 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-hexane. Yield 56 mg, m.p. 230°-232° C (decompn.)

(b) An analogous experiment of (a) by using DMF and bromoacetyl chloride instead of dimethyl sulfoxide and acetyl chloride, respectively, provided 55 mg of the pure product after the similar treatment.

(c) An analogous experiment of (a) by using DMF and methacryloyl chloride (60 mg) instead of dimethyl sulfoxide and acetyl chloride, respectively, provided 51 mg of the pure product after the similar treatment.

(d) An analogous experiment of (a) by using dimethyl sulfoxide-hexamethylphosphoramide (1 : 1) and succinyl chloride (60 mg) instead of dimethyl sulfoxide and acetyl chloride, respectively, provided 50 mg of the pure product after the similar treatment.

(e) An analogous experiment of (a) by using DMF-dichloromethane (2 : 1) and coumaryl chloride (40 mg) instead of dimethyl sulfoxide and acetyl chloride, respectively, provided 51 mg of the pure product after the similar treatment.

EXAMPLE 106

Preparation of dexamethasone 17-valerate 21-chloride (21-chloro-9α-fluoro-16α-methyl-17α-valeryloxy-pregna-1,4-diene-11β-hydroxy-3,20dione)

(a) To a solution of dexamethasone 17,21-methyl orthovalerate (9α-fluoro-16α-methyl-17-α-21-(1'-butyl-1'-methoxy-methylenedioxy)-pregna-1,4-diene11β-hydroxy-3,20-dione) (30 mg, m.p. 157°-161° C) dissolved in hexamethylphosphoramide-dichloromethane (2 : 1), acetyl chloride (0.05 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-hexane. Yield 26 mg, m.p. 193°-195° C.

(b) An analogous experiment of (a) by using DMF and benzoyl chloride instead of hesamethylphosphoramide-dichloromethane (2 : 1) and acetyl chloride respectively, provided 25 mg of the pure product after the similar treatment.

(c) Analogous experiment of (b) by using 2-phenoxypropionyl chloride instead of benzoyl chloride provided 26 mg of the pure product after the similar treatment.

(d) An analogous experiment of (b) by using 4-phenyl-butyryl chloride instead of benzoyl chloride provided 25 mg of the pure product after the similar treatment.

EXAMPLE 107

Preparation of betamethasone 17-acetate 21-chloride (17α-acetoxy-21-chloro-9α-fluoro-16β-methyl-pregna-1,4-diene-11β-hydroxy-3,20-dione)

(a) To a solution of betamethasone 17,21-methyl orthoacetate (9α-fluoro-16β-methyl-17α,21-(1'-methoxy-1'-methyl-methylenedioxy)-pregna-1,4 - diene - 11β-hydroxy-3,20-dione) (60 mg, m.p. 156–157° C) dissolved in DMF (1.2 ml), acetyl chloride (0.12 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-hexane. Yield 57 mg, m.p. 226°-229° C.

(b) An analogous experiment of (a) by using chloroacetyl chloride instead of acetyl chloride provided 56 mg of the pure product after the similar treatment.

(c) When the similar procedure as described in (a) was carried out by using DMF-dimethyl sulfoxide-chloroform (2 : 2 : 1) and oleoyl chloride instead of DMF and acetyl chloride, respectively, and the reaction mixture was treated for 80 min, the pure product was obtained in the 55 mg yield.

(d) An annalogous experiment of (a) by using 3-phenyl-propionyl chloride instead of acetyl chloride provided 53 mg of the pure product by the similar treatment.

(e) An analogous experiment of (a) by using dimethyl sulfoxide and 2-phenylbutyryl chloride instead of DMF and acetyl chloride, respectively, provided 54 mg of the pure product after the similar treatment.

EXAMPLE 108

Preparation of betamethasone 17-propionate 21-chloride (21-chloro-9α-fluoro-16β-methyl-17α-propionyloxy-pregna-1,4-diene-11β-hydroxy-3,20-dione)

(a) To a solution of betamethasone 17,21-ethyl orthopropionate (9α-fluoro-16β-methyl-17α,21-(1'-ethyl-1'-ethoxy-methylenedioxy)-pregna-1,4-diene-11β-hydroxy-3,20-dione) (60 mg, m.p. 208–211° C) dissolved in DMF(1.2 ml), acetyl chloride (0.1 ml) was added. The reaction mixture was allowed to stand at rrom temperature for 60 min. The reaction mixture was then poured into ice-water and extracted with chloroform-dichloromethane(1:1). The extract was wwashed with 2% sodium bicarbonate soln., then thoroughly with water, dried over sodium sulfate and concentrated in vacuo to give the crude product, which was recrystallized from acetone-hexane. Yield 57 mg, m.p. 193°-196° C.

(b) An analogous experiment of (a) by using bromoacetyl chloride instead of acetyl chloride provided 55 mg of the pure product after the similar treatment.

(c) An analogous experiment of (a) by using cyclohexanecarbonyl chloride instead of acetyl chloride provided 53 mg of the pure product after the similar treatment.

(d) An analogous experiment of (a) by using DMF-N-methylpyrrolidonedichloromethane (2:2:1) and propionyl chloride instead of DMF and acetyl chloride, respectively, provided 54 mg of the pure product after the similar treatment.

(e) An analogous experiment of (a) by using n-pentanecarbonyl chloride instead of acetyl chloride provided 55 mg of the pure product after the similar treatment.

(f) An analogous experiment of (a) by using dimethyl sulfoxide and p-phthaloyl chloride instead of DMF and acetyl chloride, respectively, provided 52 mg of the pure product after the similar treatment.

(g) An analogous experiment of (a) by using DMF-chloroform (2 : 1) and p-phthaloyl chloride, monomethyl ester (60 mg) instead of DMF and acetyl chloride, respectively, provided 51 mg of the pure product by the preparative thin-layer chromatographic separation after the similar treatment.

(h) An analogous experiment of (a) by using 3-methyl-3-phenyl-propionyl chloride instead of acetyl chloride provided 48 mg of the pure product after the similar treatment.

(i) When the similar procedure as described in (a) was carried out by using benzoyl chloride instead of acetyl chloride, and the reaction mixture was treated for 80 min. the crude product was obtained. The crude product was recrystallized from acetone-hexane mixture to give 54 mg of the pure product after the preparative thin-layer chromatographic separation.

EXAMPLE 109

Preparation of betamethasone 17-isobutyrate 21-chloride
(21-chloro-9α-fluoro-17α-isobutyryloxy-16β-methyl-pregna-1,4-diene-11β-hydroxy-3,20-dione)

(a) To a solution of betamethasone 17,21-methyl orthoisobutyrate (9α-fluoro- 16β-methyl-17α,21-(1′-isopropyl-1′-methyl-methylenedioxy)-pregna - 1,4 - diene-11β-hydroxy-3,20-dione) (60 mg, m.p. 173° C) dissolved in DMF (1.2 ml), acetyl chloride (0.1 ml) was added. The reaction mixture was allowed to stand at room temperature for 60 min. The reaction mixture was then poured into icewater and extracted with chloroformdichloromethane (1 : 1). The extract was washed with 2% sodium bicarbonate soln., then thoroughly with water, dried over sodium sulfate and concentrated in vacuo to give the crude product, which was recrystallized from aceton-hexane. Yield 55 mg, m.p. 193°–194° C.

(b) An analogous experiment of (a) by using 3-methyl-4-phenyl-butyryl chloride instead of acetyl chloride provided the crude product by the similar treatment. The crude product was recrystallized from acetone-hexane to give 52 mg of the pure product after the preparative thin-layer chromatographic separation.

(c) An analogous experiment of (b) by using 4-methyl-4-phenyl-butyryl chloride instead of 3-methyl-4-phenyl-butyryl chloride provided 51 mg of the pure product after the similar treatment.

(d) When the similar procedure as described in (a) was carried out by using oxaloyl chloride instead of acetyl chloride, and the reaction mixture was treated for 45 min., the pure product was obtained in the 50 mg yield.

EXAMPLE 110

Preparation of betamethasone 17-valerate 21-chloride
(21-chloro-9α-fluoro-16β-methyl-17α-valeryloxy-pregna-1,4-diene-11β-hydroxy-3,20-dione)

(a) To a solution of betamethasone 17,21-methyl orthovalerate (9α-fluoro-16β-methyl-17α,21-(1′-butyl-1′-methoxy-methylenedioxy)-pregna-1,4-diene-11β-hydroxy-3,20-dione) (60 mg, m.p. 152°–154° c) dissolved in DMF (1.2 ml) acetyl chloride (0.12 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-hexane-isopropyl ether. Yield 55 mg, m.p. 197°–210° c.

(b) When the similar procedure as described in (a) was carried out by using DMF-dichloromethane (1 : 1) and dichloroacetyl chloride instead of DMF and acetyl chloride, respectively, and the reaction mixture was treated for 55 min, the pure product was obtained in the 51 mg yield.

(c) An analogous experiment of (a) by using butyryl chloride instead of acetyl chloride provided 51 mg of the pure product after the similar treatment.

(d) An analogous experiment of (a) by using pivaloyl chloride instead of acetyl chloride provided 51 mg of the pure product after the similar treatment.

(e) An analogous experiment of (a) by using m-methylbenzoyl chloride instead of acetyl chloride provided 48 mg of the pure product after the similar treatment.

EXAMPLE 111

Preparation of betamethasone 17-isovalerate 21-chloride (21-chloro-9α-fluoro-17-isovalerate 21-chloride
(21-chloro-9α-fluoro-17α-isovaleryloxy-16β-methyl-pregna-1,4-diene-11β-hydroxy-3,20-dione)

(a) To a solution of betamethasone 17,21-methyl orthoisovalerate (9α-fluoro16β-methyl-17α,21-(1′-isobutyl-1′-methoxy-methylenedioxy)-pregna-1,4-diene-11β-hydroxy-3,20-dione) (30 mg, m.p. 175–176° c) dissolved in DMF (0.8 ml), acetyl chloride (0.05 ml) was added. The reaction mixture was allowed to stand at room temperature for 70 min. The reaction mixture was then poured into ice-water and extracted with dichloromethane. The extract was washed with 2% sodium bicarbonate soln., then thoroughly with water, dried over sodium sulfate and concentrated in vacuo to give the crude product, which was recrystallized from acetone-hexane mixture. Yield 27 mg, m.p. 231°–233° c.

(b) When the similar procedure as described in (a) was carried out by using DMF dichloromethane (2 : 1) and succinyl chloride (50 mg) instead of DMF and acetyl chloride, respectively, and the reaction mixture treated for 50 min., the pure product was obtained in the 25 mg yield.

(c) When the similar procedure as described in (a) was carried out by using 2-chloro-4-nitro-benzoyl chloride (50 mg) instead of acetyl chloride, and the reaction mixture was treated for 70 min., the pure product was obtained in the 25 mg yield.

EXAMPLE 112

Preparation of betamethasone 17-caproate 21-chloride (17α-caproyloxy-21-chloro-16β-methyl-pregna-1,4-diene-11β-hydroxy-3,20-dione)

(a) To a solution of betamethasone 17,21-methyl orthocaproate (9α-fluoro-16β-methyl-17α,21-(1'-methoxy-1'-pentyl-methylenedioxy)-pregna-1,4-diene-11β-hydroxy-3,20-dione) (30 mg, m.p. 148°–151° c) dissolved in DMF (0.5 ml), acetyl chloride (0.05 ml) dissolved in chloroform (0.2 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-ether. Yield 26.5 mg, m.p.

(b) An analogous experiment of (a) by using propionyl chloride instead of acetyl chloride provided 26 mg of the pure product after the similar treatment.

(c) An analogous experiment of (a) by using cinnamoyl chloride instead of acetyl chloride provided 25 mg of the pure product after the similar treatment.

EXAMPLE 113

Preparation of betamethasone 17-cyclopentanecarboxylate 21-chloride (21-chloro-17α-cyclopentanecarbonyloxy-9α-fluoro-16β-methyl-pregna-1,4-diene-11β-hydroxy-3,20-dione)

(a) To a solution of betamethasone 17,21-methyl orthocyclopentanecarboxylate (21-chloro-9α-fluoro-16β-methyl-17α,21-(1'-cyclopentyl-1'-methoxy-methylenedioxy)-pregna-1,4-diene-11β-hydroxy-3,20-dione) (60 mg, m.p. 163°–167° c) dissolved in DMF (1.5 ml), acetyl chloride (0.1 ml) was added. The reaction mixture was allowed to stand at room temperature for 60 min. The reaction mixture was then poured into ice-water and extracted with chloroform. The extract was washed with 2% sodium bicarbonate soln., then thoroughly with water, dried over sodium sulfate and concentrated in vacuo to give the crude product, which was recrystallized from acetone-ether. Yield 54 mg, m.p. 228°–231° c.

(b) In an analogous experiment of (a), when DMF-dry benzene (1:1) (2 ml) and propionyl chloride (0.1 ml) were used instead of DMF and acetyl chloride, respectively, and the reaction mixture was refluxed for 10 min., the reaction mixture was diluted with chloroform, poured into ice-water and extracted with chloroform. The extract was then washed with 2% sodium bicarbonate soln., water, dried over sodium sulfate and concentrated in vacuo to give the crude product, which was recrystallized from acetone-ether. Yield 50 mg.

(c) An analogous experiment of (a) by using cyclohexanecarbonyl chloride instead of acetyl chloride provided 51 mg of the pure product after the similar treatment.

EXAMPLE 114

Preparation of betamethasone 17-benzoate 21-chloride (21-chloro-9α-fluoro-16β-methyl-17α-benzoyloxy-pregna-1,4-diene-11β-hydroxy-3,20-dione)

(a) To a solution of betamethasone 17,21-methyl orthobenzoate (9α-fluoro-16β-methyl-17α,21-(1'-methoxy-1'-phenyl-methylenedioxy)-pregna-1,4-diene-11β-hydroxy-3,20-dione) (60 mg, m.p. 167°–172° c) dissolved in DMF (1.5 ml), acetyl chloride (0.1 ml) was added. The reaction mixture was allowed to stand at room temperature for 80 min. The reaction mixture was then poured into ice-water and extracted with chloroform. The extract was washed with 2% sodium bicarbonate soln., then thoroughly with water, dried over sodium sulfate and concentrated in vacuo to give the crude product which was recrystallized from acetone-hexane-isopropyl ether mixture. Yield 55 mg, m.p. 233°–237° c.

(b) In an analogous experiment of (a), when the reaction mixture was stirred at 80° c for 10 min. by the similar treatment, the pure product was obtained in the 48 mg yield.

(c) An analogous experiment of (a) by using propionyl chloride instead of acetyl chloride provided 53 mg of the pure product by the similar treatment.

(d) When the similar procedure as described in (a) was carried out by using benzoyl chloride instead of acetyl chloride, and the reaction mixture was treated for 80 min, the pure product was obtained in the 50 mg yield.

(e) An analogous experiment of (a) by using phenylacetyl chloride instead of acetyl chloride provided 49 mg of the pure product by the similar treatment.

(f) An analogous experiment of (a) by using n-heptanoyl chloride instead of acetyl chloride provided 51 mg of the pure product by the similar treatment.

(g) An analogous experiment of (a) by using succinoyl chloride instead of acetyl chloride provided 50 mg of the pure product by the similar treatment.

EXAMPLE 115

Preparation of 17α-acetoxy-21-chloro-pregn-4-ene-3,20-dione

To a solution of 17α,21-(1'-methoxy-1'-methyl-methylenedioxy)-pregn-4-ene-3,20-dione (30 mg, m.p. 175°–177° C) dissolved in DMF (1.2 ml), butyryl chloride (0.1 ml) was added. The reaction mixture was allowed to stand at room temperature for 70 min. The reaction mixture was then poured into ice-water and extracted with chloroform. The extract was washed with dil. sodium bicarbonate soln., then thoroughly with water, dried over sodium sulfate and concentrated in vacuo to give the crude product, which was recrystallized from acetone. Yield 26 mg, m.p. 218°–221° C.

EXAMPLE 116

Preparation of 17α-acetoxy-21-chloro-9β,11β-oxido-pregn-4-ene-3,20-dione

To a solution of 17α,21-(1'-methoxy-1'-methyl-methylenedioxy)-9β,11β-oxido-pregn-4-ene-3,20-dione (30 mg, m.p. 157°–161° C) dissolved in DMF (1.2 ml), propionyl chloride (0.1 ml) was added. The reaction mixture was allowed to stand at room temperature for 65 min. Then the reaction mixture was treated by the similar procedure as described in Example 115 to give the crude product, which was recrystallized from acetone-hexane. Yield 26 mg, m.p. 196°–199° C.

EXAMPLE 117

Preparation of 17α-benzoyloxy-21-chloro-16β-methyl-9β,11β-oxido-pregna-1,4-diene-3,20-dione To a solution of 16β-methyl-17α,21-(1'-methoxy-1'-phenyl-methylenedioxy)-9β,11β-oxido-pregna-1,4-diene-3,20-dione (30 mg, m.p. 148°–150° C) dissolved in dimethyl sulfoxide (1.5 ml), isobutyryl chloride (0.13 ml) was added. The reaction mixture was allowed to stand at room temperature for 80 min. Then the reaction mixture was treated by the similar procedure as described in Example 115 to give the crude product, which was recrystallized from acetone-hexane-isopropyl ether. Yield 25 mg, m.p. 146°–149° C.

EXAMPLE 118

Preparation of 21-chloro-6α,9α-difluoro-17α-propionyloxy-pregna-1,4-diene-11β-hydroxy-3,20-dione To a solution of 6α,9α-difluoro-17α,21-(1'-ethyl-1'-methoxy-methylenedioxy)-pregna-1,4-diene-11β-hydroxy-3,20-dione (30 mg, m.p. 187°–189° C) dissolved in DMF (1.5 ml), acetyl chloride (0.13 ml) was added. The reaction mixture was allowed to stand at room temperature for 50 min. Then the reaction mixture was treated by the similar procedure as described in Example 115 to give the crude product, which was recrystallized from acetone-ether. Yield 26 mg, m.p. 227°–229° C.

EXAMPLE 119

Preparation of 9α,21-dichloro-16α-methyl-17α-propionyloxy-pregna-1,4-diene-11β-hydroxy-3,20-dione To a solution of 9α-chloro-16α-methyl-17α,21-(1'-ethyl-1'-methoxy-methylenedioxy)-pregna-1,4-diene-11β-hydroxy-3,20-dione (30 mg, m.p. 174°–178° C) dissolved in DMF-chloroform (2:1) (1.5 ml), propionyl chloride (0.13 ml) was added. The reaction mixture was allowed to stand at room temperature for 60 min. Then the reaction mixture was treated by the similar procedure as described in Example 115 to give the crude product, which was recrystallized from ethyl acetate-hexane. Yield 25 mg, m.p. 202°–205° C.

EXAMPLE 120

Preparation of 17α-acetoxy-9α,21-dichloro-16β-methyl-pregna-1,4-diene-11β-hydroxy-3,20-dione To a solution of 9α-chloro-16β-methyl-17α,21-(1'-methoxy-1'-methyl-methylenedioxy)-pregna-1,4-diene-11β-hydroxy-3,20-dione (60 mg, m.p. 165°–168° C) dissolved in DMF-dimethyl sulfoxide-dichloromethane (2:2:1) (3 ml), butyryl chloride (0.2 ml) was added. The reaction mixture was allowed to stand at room temperature for 60 min. The reaction mixture was then poured into ice-water and extracted with dichloromethane. The extract was washed with dil. sodium bicarbonate soln. and water, dried over sodium sulfate and concentrated in vacuo to give the crude product, which was recrystallized from acetone-hexane. Yield 55 mg, m.p. 230°–233° C. (decompn.)

EXAMPLE 121

Preparation of 21-chloro-9α-fluoro-11β-hydroxy-17α-valeryloxy-pregn-4-ene-3,20-dione To a solution of 9α-fluoro-17α,21-(1'-butyl-1'-methoxy-methylenedioxy)-pregna-4-ene-11β-hydroxy-3,20-dione (60 mg, m.p. 172°–175° C) dissolved in DMF-N-methylpyrrolidone (1:1) (1.6 ml), butyryl chloride (0.13 ml) was added. The reaction mixture was allowed to stand at room temperature for 70 min. Then the reaction mixture was treated by the similar procedure as described in Example 120 to give 54 mg, m.p. 210°–211° C of the pure product.

EXAMPLE 122

Preparation of 16α,17α-diacetoxy-21-chloro-9α-fluoro-pregna-1,4-diene-11β-hydroxy-3,20-dione To a solution of 16α-acetoxy-9α-fluoro-17α,21-(1'-ethoxy-1'-methyl-methylenedioxy)-pregna-1,4-diene-3,20-dione (30 mg, m.p. 193°–195° C) dissolved in DMF 91.5 ml), acetyl chloride (0.1 ml) was added. The reaction mixture was allowed to stand at room temperature for 60 min. The reaction mixture was then poured into ice-water and extracted with chloroform. The extract was washed with dil. sodium bicarbonate soln. and water, dried over sodium sulfate and concentrated in vacuo to give the crude product, which was recrystallized from chloroform-methanol. Yield 26 mg, m.p. 296°–299° C.

EXAMPLE 123

Preparation of 17α-acetoxy-21-chloro-9α-fluoro-16α-methoxy-pregn-4-ene-3,20-dione To a solution of 9α-fluoro-16α-methoxy-17α,21-(1'-ethoxy-1'-methyl-methylenedioxy)-pregna-4-ene-3,20-dione (15 mg, m.p. 191°–195° C) dissolved in dimethyl sulfoxide (0.3 ml), propionyl chloride (0.02 ml) was added. The reaction mixture was allowed to stand at room temperature for 60 min. The reaction mixture was then subjected to preparative thin-layer chromatography directly to give 12 mg, m.p. 241°–244° C of the pure product.

EXAMPLE 124

Preparation of betamethasone 17-acetate 21-bromide (17α-acetoxy-21-bromo-16β-methyl-pregna-1,4-diene-11β-hydroxy-3,20-dione)

(a) To a solution of betamethasone 17,21-methyl orthoacetate (30 mg) dissolved in DMF (0.8 ml), acetyl bromide (0.1 ml) was added. The reaction mixture was allowed to stand at room temperature for 50 min. The reaction mixture was then poured into ice-water and extracted with chloroform. The extract was washed with dil. sodium bicarbonate soln. and water, dried over sodium sulfate and concentrated in vacuo to give the crude product, which was recrystallized from ethyl acetate-hexane. Yield 26 mg., m.p. 210°–212° C.

(b) An analogous experiment of (a) by using dimethyl sulfoxide-chloroform (5:1) and n-valeryl bromide instead of DMF and acetyl bromide, respectively, provided 26 mg of the pure product after the similar treatment.

EXAMPLE 125

Preparation of betamethasone
17-propionate-21-bromide
(21-bromo-9α-fluoro-16β-methyl-17α-propionyloxy-
pregna-1,4-diene-11β-hydroxy-3,20-dione)

(a) To a solution of betamethasone 17,21-ethyl orthopropionate (30 mg) dissolved in DMF (0.8 ml), acetyl bromide (0.05 ml) was added. The reaction mixture was allowed to stand at room temperature for 50 min. The reaction mixture was then treated by the similar procedure as described in Example 124 (a) to give the crude product, which was recrystallized from acetone-hexane. Yield 25 mg, m.p. 204°–206° C.

(b) An analogous experiment of (a) by using bromoacetyl bromide instead of acetyl bromide provided 24 mg of the pure product after the similar treatment.

(c) An analogous experiment of (a) by using isobutyryl bromide instead of acetyl bromide provided 22 mg of the pure product after the similar treatment.

EXAMPLE 126

Preparation of betamethasone 17-isobutyrate
21-bromide
(21-bromo-9α-fluoro-17α-isobutyryloxy-16β-methyl-
pregna-1,4-diene-11β-hydroxy-3,20-dione)

(a) To a solution of betamethansone 17,21-methyl orthoisobutyrate (30 mg) dissolved in DMF (1 ml), isobutyryl bromide (0.08 ml) was added. The reaction mixture was allowed to stand at room temperature for 55 min. The reaction mixture was then poured into ice-water and extracted with chloroform. The extract was washed with dil. sodium bicarbonate soln. and water, dried over sodium sulfate and concentrated in vacuo to give the crude product, which was recrystallized from ethyl acetate-hexane. Yield 25 mg, m.p. 183°–185° C.

(b) An analogous experiment of (a) by using acetyl bromide instead of isobutyryl bromide provided 23 mg of the pure product after the similar treatment.

EXAMPLE 127

Preparation of betamethasone 17-butyrate 21-bromide
(21-bromo-17α-butyryloxy-9α-fluoro-16β-methyl
-pregna-1,4-diene-11β-hydroxy-3,20-dione)

To a solution of betamethasone 17,21-methyl orthobutyrate (300 mg) dissolved in DMF (1 ml), acetyl bromide (0.08 ml) was added. Then the reaction mixture was treated by the similar procedure as described in Example 126 (a) to give 24 mg (m.p. 184°–185° C) of the pure product.

EXAMPLE 128

Preparation of
17α-acetoxy-21-bromo-9α-chloro-16β-methyl-pregna-
1,4-diene-11β-hydroxy-3,20-dione To a solution of 9α-chloro-16β-methyl-17α,21-(1′-methoxy-1′-methyl-methylenedioxy)-pregna-1,4-diene-11β-hydroxy-3,20-dione (30 mg) dissolved in hexamethylphosphoramide-dichloromethane (3:1) (1 ml), acetyl bromide (0.08 ml) was added. The reaction mixture was allowed to stand at room temperature for 50 min. The reaction mixture was then treated by the similar procedure as described in Example 126 (a) to give the crude product, which was recrystallized from acetone-hexane. Yield 23 mg, m.p. 213°–216° C. (dec.)

EXAMPLE 129

Preparation of dexamethasone 17-propionate
21-bromide(21-bromo-9α-fluoro-16α-methyl-17α-pro-
pionyloxy-pregna-1,4-diene-11β-hydroxy-3,20-dione)

(a) To a solution of dexamethasone 17,21-ethyl orthopropionate (30 mg) dissolved in DMF (1ml), acetyl bromide (0.08 ml) was added. The reaction mixture was allowed to stand at room temperature for 50 min. The reaction mixture was then poured into ice-water and extracted with chloroform. The extract was washed with dil. sodium bicarbonate soln. and water, dried over sodium sulfate and concentrated in vacuo to give the crude product, which was recrystallized from acetone-hexane. Yield 24 mg, m.p. 225°–227° C (dec.)

(b) An analogous experiment of (a) by using crotonyl bromide instead of acetyl bromide provided 22 mg of the pure product after the similar treatment.

(c) An analogous experiment of (a) by using dimethyl sulfoxide and n-valeryl chloride instead of DMF and acetyl bromide, respectively, provided the crude product by the similar treatment. The crude product was recrystallized from ethanol to give 23 mg of the pure product.

EXAMPLE 130

Preparation of dexamethasone 17-butyrate 21-bromide
(21-bromo-17α-butyryloxy-9α-fluoro-16α-methyl-preg-
na-1,4-diene-11β-hydroxy-3,20-dione)

To a solution of dexamethasone 17,21-methyl orthobutyrate (30 mg) dissolved in DMF (1 ml), acetyl bromide (0.08 ml) was added. The reaction mixture was allowed to stand at room temperature for 50 min. Then the reaction mixture was treated by the similar procedure as described in Example 129 (a) to give 24 mg of the pure product.

EXAMPLE 131

Preparation of betamethasone 17-acetate 21-iodide
(17α-acetoxy-9α-fluoro-21-iodo-11β-hydroxy-16β-
methyl-pregna-1,4-dien-3,20-dione)

To a solution of 30 mg betamethasone 17,21-methyl orthoacetate in 1 ml DMF 0.08 ml of acetyl iodide was added. After keeping at room temperature for 50 min. the reaction mixture was poured into ice-water and was extracted with dichloromethane. The extract was washed with dil. NaHCO₃ sol. and water, dried over Na₂SO₄, and then was evaporated in vacuo to give the crude product. The pure one (m.p. 168°–171° C) was obtained by recrystallization from acetone-hexane in the 24 mg yield.

EXAMPLE 132

Preparation of betamethasone 17-propionate 21-iodide
(9α-fluoro-21-iodo-11β-hydroxy-16β-methyl-17α-pro-
pionyloxy-pregna-1,4-dien-3,20-dione)

To a solution of 30 mg of betamethasone 17,21-methyl orthobutyrate in 1 ml of DMF, 0.09 ml of acetyl iodide was added. The reaction mixture was allowed to stand at room temperature for 50 min., and was treated by the similar method as described in Example 131. The pure product (m.p. 167°–169° C) was obtained by recrystallization of the crude one thus obtained from ethyl acetate-hexane in the 24 mg yield.

EXAMPLE 133

Preparation of betamethasone 17-butyrate 21-iodide (17α-butyryloxy-9α-fluoro-11β-hydroxy-21-iodo-16β-methyl-pregna-1,4-dien-3,20-dione)

To a solution of 30 mg of betamethasone 17,21-methyl orthobutyrate in 1 ml of DMF, 0.08 ml of acetyl iodide was added. When the mixture was reacted in the similar manner as described in Example 132, the pure product (m.p. 161°–163° C) was obtained in the 24 mg yield.

EXAMPLE 134

Preparation of dexamethasone 17-propionate 21-iodide (9α-fluoro-11β-hydroxy-21-iodo-16α-methyl-17α-propionyloxy-pregna-1,4-dien-3,20-dione)

To a solution of 30 mg of dexamethasone 17,21-ethyl orthopropionate in 1 ml of DMF, 0.09 ml of acetyl iodide was added. After keeping at room temperature for 50 min., the reaction mixture was poured into ice-water and extracted with chloroform. The extract was washed with aq. $NaHCO_3$ solution and water and dried over $Na_2SO_4$. Evaporation of the solvent gave the crude product. The pure one (m.p. 220°–223° C (dec.)) was obtained by recrystallization from acetone-hexane in the 25 mg yield.

EXAMPLE 135

Preparation of hydrocortisone 17-acetate 21-chloride (17α-acetoxy-21-chloro-4-pregnen-11β-01, 3, 20-dione)

To a mixture of 100 mg. of hydrocortisone, 17, 21-methyl orthoacetate (17α,21-(1'-methyl-1'-methoxy-methylenedioxy)-4-pregnen-11β-ol-3,20-dione) in 5.0 ml of dimethylformamide (DMF), 0.1 ml of phosphorus oxychloride ($POCl_3$) was added. The mixture was allowed to stand for 20 min. at room temperature. Then, this was evaporated in vacuo to gave a white solid. This was crystallized from aceton-n-hexane-isopropylether to give 85 mg of the product, m.p. 252°14 254° C.

EXAMPLE 136

Preparation of hydrocortisone 17-propionate 21-chloride(21-chloro-17α-propionyloxy-4-pregnene-11β-ol-3,20-dione)

To a mixture of 100 mg of hydrocortisone, 17,21-ethylorthopropionate (17α,21-(1'-ethyl-1'-ethoxy-methylenedioxy)-4-pregnen-11β-ol-3,20-dione) (m.p. 182.5–183.5°)in 5 ml. of DMF, 0.1 ml of phosphorus oxychloride was added. The mixture was allowed to stand for 20 min. at room temperature, and then was evaporated in vacuo to give a residue. This was crystallized from acetone to give 87 mg of the product, m.p. 225°–227° C.

EXAMPLE 137

Preparation of hydrocortisone 17-butyrate 21-chloride (17α-butyryloxy-21-chloro-11β-hydroxy-4-pregnene-3,20-dione)

To a solution of 100 mg of hydrocortisone 17,21-methyl orthobutyrate (17α,21-(1'-methoxy-1'-propyl-methylenedioxy)-11β-hydroxy-4-pregnen-3,20-dione) in 5 ml of DMF, 0.1 ml of phosphorus oxychloride was added. The mixture was allowed to stand at room temperature for 20 min. and was evaporated in vacuo, to yield the crude product. Recrystallization from aceton-n-hexane afforded 92 mg of the pure product, m.p. 192°–196° C.

EXAMPLE 138

Preparation of hydrocortisone 17-valerate 21-chloride (21-chloro-11β-hydroxy-17α-valeroyloxy-4-pregnen-3,20-dione)

To a solution of 100 mg of hydrocortisone 17,21-methyl orthovalerate (17α-21-(1'-butyl-1'-methoxy-methylenedioxy)-11β-hydroxy-4-pregnen-3,20-dione) in 5 ml of DMF, 0.1 ml of phosphorus oxychloride was added. The mixuture was allowed to stand at room temperature for 30 min., and this was evaporated in vacuo to give the crude product. The product was recrystallized from aceton-n-hexane-isopropylether to afford 90 mg of the colorless needles. m.p. 154°–156° C.

EXAMPLE 139

Preparation of hydrocortisone 17-caproate 21-chloride (17α-caproyloxy-21-chloro-11β-hydroxy-4-pregnen-3,20-dione)

To a mixture of 100 mg of hydrocortisone-17,21-methyl orthocaproate (17α,21-(1'-methoxy-1'-pentyl-methylenedioxy)-11β-hydroxy-4-pregnen-3,20-dione) (m.p. 119°–120° ) in 5 ml of DMF, 0.1 ml of phosphorus oxychloride was added. The mixture was allowed to stand at room temperature for 30 min., and this was evaporated in vacuo to give the crude product. By recrystallization from acetone-hexane-isopropylether, the pure product was obtained, yield 89 mg, m.p. 163°–167 ° C.

EXAMPLE 140

Preparation of hydrocortisone 17-benzoate 21-chloride (17α-benzoyloxy-21-chloro-11β-hydroxy-4-pregnen-3,20-dione)

To a solution of 100 mg of hydrocortisone 17,21-methyl orthobenzoate (17α-21-(1'-methoxy-1'-pehnyl-methylenedioxy)-11β-hydroxy-4-pregnene-3,20-dione) (m.p. 208°–210° C) in 5 ml of DMF, 0.1 ml of phosphorus oxychloride was added. The mixture was allowed to stand at room temperature for 40 min. Then, this was evaporated in vacuo to give the crystalline product. Recrystalization of this from acetone-n-hexane gave the pure product, yield 88 mg, m.p. 226°–229° C.

EXAMPLE 141

Preparation of hydrocortisone 17-cyclopentanecarboxylate 21-chloride (17α-cyclopentanecarbonyloxy-21-chloro-11β-hydroxy-4-pregnene-3,20-dione)

To a mixture of 100 mg of hydrocortisone 17,21-methyl orthocyclopentane-carboxylate (17β,21-(1'-cyclopentyl-1'-methoxy-methyenedioxy)-11β-hydroxy-4-pregnen-3,20-dione) (m.p. 197°–201° C) in 15 ml of DMF, 0.1 ml of phosphorus oxychoride was added. The mixture was allowed to stand for 45 min. at room temperature, and then was evaporated in vacuo to give a crude product. This was recrystallized from acetone-n-hexane-isopropylether to afford the colorless needles, yield 89 mg, m.p. 229°–233° C.

EXAMPLE 142

Preparation of prednisolone 17-propionate 21-chloride (21-chloro-17-α-propionyloxy-11β-hydroxy-pregna-1,4-diene-3,20-dione)

To a solution of 100 mg of prednisolone 17,21-ethyl orthopropionate (17α,21-(1'-ethyl-1'-ethoxy-methylenedioxy)-11β-hydroxy-pregna-1,4-dien-3,20-dione) (m.p. 180°–184° C) in 5 ml of DMF, 0.1 ml of phosphorus oxychloride was added. The reaction mixture was allowed to stand for 30 min. at room temperature, and then was evaporated in vacuo to give a crude product. This was recrystallized from aceton to give the pure product, yield 92 mg, m.p. 225°–227° C.

EXAMPLE 143

Preparation of prednisolone 17-butyrate 21-chloride (21-chloro-17-butyryloxy-pregna-1,4-dien-11β-ol-3,20-dione)

To a mixture of 100 mg of prednisolone 17,21-methyl orthobutyrate (17α,21-(1'-methoxy-1'-propyl-methylenedioxy)-11β-ol-pregna-1,4-diene-3,20-dione) in 5 ml of DMF, 0.1 ml of phosphorus oxychloride was added. The reaction mixture was allowed to stand for 30 min. at room temperature, and then was evaporated in vacuo to give the crude product. This was crystallized from acetone-hexane to afford 91 mg of pure product, m.p. 197°–200° C.

EXAMPLE 144

Preparation of prednisolone 17-valerate 21-chloride (21-chloro-17α-valeroyloxy-11β-hydroxy-pregna-1,4-dien-3,20-dione)

To a solution of 100 mg of prednisolone 17,21-methyl orthovalerate (17α,21-(1'-butyl-1'-methoxy-methylenedioxy)-11β-hydroxy-pregna-1,4-dien-3,20-dione) in 5 ml of DMF, 0.1 ml of phosphorus oxychloride was added. The reaction mixture was allowed to stand for 30 min. at room temperature, and was evaporated in vacuo to give a crude product. This was recrystallized from acetone-hexane-isopropylether to give 91 mg of the pure product, m.p. 191°–193° C.

EXAMPLE 145

Preparation of prednisolone 17-caproate 21-chloride (17α-caproyloxy-21-chloro-11β-hydroxy-pregna-1,4-dien-3,20-dione)

To a mixture of 100 mg of prednisolone 17,21-methyl orthocaproate (17α,21-(1'-methoxy-1'-pentyl-methylenedioxy)-11β-hydroxy-pregna-1,4-dien-3,20-dione) (m.p. 137°–141° C) in 5 ml of DMF, 0.1 ml of phosphorus oxychloride was added. The reaction mixture was allowed to stand for 45 min. at room temperature, and then was evaporated in vacuo to give the crude product. Pure product, m.p. 199°–201° C, was obtained by recrystallizaton from acetone-hexane-isopropyl ether in 90 mg yield.

EXAMPLE 146

Preparation of dexamethasone 17-propionate 21-chloride (21-chloro-9α-fluoro-11β-hydroxy-16β-methyl-17β-propionyloxy-pregna-1,4-dien-3,20-dione)

To a solution of 100 mg of dexamethasone 17,21-ethyl orthopropionate (9α-fluoro-17α,21-(1'-ethyl-1'-ethoxymethylenedioxy)-11β-hydroxy-16α-methylpregna-1,4-dien-3,20-dione) (m.p. 219–221α) in 8 ml of DMF, 0.12 ml of phosporus oxychloride was added. After keeping at room temperature for 40 min., the reaction mixture was evaporated in vacuo to give the crude product. Pure one, m.p. 240°–243° C was obtained by recrystallization from acetone-hexane in 91 mg yield.

EXAMPLE 147

Preparation of dexamethasone 17-butyrate 21-chloride (17α-butyroyloxy-21-chloro-9β-fluoro-11β-hydroxy-16α-methyl-pregna-1,4-dien-3,20 -dione)

To a solution of 100 mg of dexamethasone 17,21-methyl orthobutyrate (9α-fluoro-16α-methyl-17α-21-(1'-methoxy-1'-propyl-methylenedioxy)-11β-hydroxy-pregna-1,4-dien-3,20-dione) (m.p. 166–169° C) in 1.5 ml of DMF, 0.12 ml of phosphorus oxychloride was added. After keeping at room temperature for 45 min., the reaction mixture was evaporated in vacuo. Recrystallization of the residue thus obtained from acetone-hexane afforded 88 mg of the pure product, m.p. 230°–232° C. (dec.).

EXAMPLE 148

Preparation of dexamethasone 17-valerate 21-chloride (21-chloro-9α-fluoro-16α-methyl-11β-hydroxy-17α-valeroyloxy-pregna-1,4-dien-3,20-dione)

To a solution of 100 mg of dexamethasone 17,21-methyl orthovalerate (9α-fluoro-11β-hydroxy-16α-methyl-17α,21-(1'-methoxy-1'-butyl-methylenedioxy)-pregna-1,4-dien-3,20-dione) (m.p. 157°–161° C) in 8 ml of DMF, 0.12 ml of phosphorus oxychloride was added. The reaction mixture was allowed to stand at room temperature for 45 min., and then was evaporated in vacuo to give the crude product. By recrystallization of this from acetone-hexane, the pure product (86 mg), m.p. 193°–196° C, was obtained.

EXAMPLE 149

Preparation of betamethasone 17-acetate 21-chloride (17α-acetoxy-21-chloro-9α-fluoro-11β-hydroxy-6β-methyl-pregna-1,4-dien-3,20-dione)

To a solution of 50 mg of betamethasone 17,21-methyl-orthoacetate (9α-fluoro-11β-hydroxy-6β-methyl-17α,21-(1'-methyl-1'-methoxy-methylenedioxy))-pregna-1,4-dien-3,20-dione) (m.p. 156°–157° C) in 3 ml of DMF, 0.06 ml of phosphorus oxychloride was added. The reaction mixture was allowed to stand at room temperature for 30 min., and then was evaporated in vacuo to give the crude product. By recrystallization of this from acetone-hexane, the pure product (46 mg), m.p. 226.5°–230° C, was obtained.

EXAMPLE 150

Preparation of betamethasone 17-propionate 21-chloride(21-chloro-9α-fluoro-11β-hydroxy-16β-methyl-17α-propionyloxy-pregna-1,4-dien-3,20-dione)

To a solution of 100 mg of betamethasone 17,21-ethyl orthopropinate (9α-fluoro-16β-methyl-11β-hydroxy-17α,21-(1'-ethyl-1'-ethoxy-methylenedioxy)-pregna-1,4-dien-3,20-dione) (m.p. 208–211° C) in 5 ml of DMF, 0.12 ml of phosphorus oxychloride was added. After keeping at room temperature for 25 min., the mixture was evaporated in vacuo to give the crude product. The pure one, m.p. 193°–196° C, was obtained by recrystallization from acetone-hexane in 91 mg yield.

EXAMPLE 151

Preparation of betamethasone 17-butyrate 21-chloride (17α-butyryloxy-21-chloro-9α-fluoro-11β-hydroxy-16β-methyl-pregna-1,4-dien-3,20-dione)

To a mixture of 50 mg of betamethasone 17,21-methyl othobutyrate (9α-fluoro-11β-hydroxy-16β-methyl-17α,21-(1'-methoxy-1'-propyl-methylenedioxy)-pregna-1,4-dien-3,20-dione) (m.p. 148° C) in 3 ml of DMF, 0.06 ml of phosphorus oxychloride was added. After keeping at room temperature for 30 min., the mixture was evaporated in vacuo to give the crude product. The pure one, m.p. 171°-173°, was obtained by recrystallization from acetone-hexane in 44 mg yield.

EXAMPLE 152

Preparation of betamethasone 17-isobutyrate 21-chloride (21-chloro-9α-fluoro-17α-isobutyryloxy-11β-hydroxy-16β-methyl-pregna-1,4-dien-3,20-dione)

To a mixture of 50 mg of betamethasone 17,21-methyl orthoisobutyrate (9α-fluoro-11β-hydroxy-16β-methyl-17α,21-(1'-isopropyl-1'-methoxy-methylenedioxy pregna-1,4-dien-3,20-dione) (m.p. 173° C) in 3 ml of DMF, 0.06 ml of phosphorus oxychloride was added. The reaction mixture was allowed to stand at room temperature for 35 min. and then, evaporated in vacuo to give the crude product. The pure one, m.p. 192°-194° C, was obtained by recrystallization from acetone-hexane in 42 mg yield.

EXAMPLE 153

Preparation of betamethasone 17-valerate 21-chloride (21-chloro-9α-fluoro-11β-hydroxy-16β-methyl-17α-valeroyloxy-pregna-1,4-dien-3,°-dione)

To a solution of 50 mg of betamethasone 17,21-methyl othovalerate (9α-fluoro-17α,21-(1'-butyl-1'-methoxy-methylenedioxy)-11β-hydroxy-16β-methyl pregna-1,4-dien-3,20-dione) (m.p. 152°-154°) in 2.8 ml of DMF, 0.06 ml of phosphorus oxychloride was added. After keeping at room temperature for 35 min. the mixture was evaporated in vacuo to give the crude product. By recrystallization from acetone-hexane-isopropylether, the pure product, m.p. 197°-201°, was obtained in 40 mg yield.

EXAMPLE 154

Preparation of betamethasone 17-isovalerate 21-chloride (21-chloro-9α-fluoro-17α-isovaleroyloxy-11β-hydroxy-16β-methyl-pregna-1,4-dien-3,20-dione)

To a solution of 50 mg of betamethasone 17,21-methyl orthoisovalerate (9α-fluoro-11β-hydroxy-17α,21-(1'-isobutyl-1'-methoxy-methylenedioxy)-16β-methyl-pregna-1,4diene-3,20-dione) (m.p. 175°-176° C) in 3 ml of DMF, 0.06 ml of phosphorus oxychloride was added. The reaction mixture was allowed to stand at room temperature for 40 min., and then was evaporated in vacuo to give the crude product. Recrystallization from acetone-hexane-isopropylether afforded 43 mg of the pure compound, m.p. 231°-233° C.

EXAMPLE 155

Preparation of betamethasone 17-caproate 21-chloride (17α-caproyloxy-21-chloro-9α-fluoro-11β-hydroxy-16β-methyl-pregna-1,4-dien-3,20-dione)

To a solution of 50 mg of betamethasone 17,21-methyl orthocaproate (9α-fluoro-11β-hydroxy-16β-methyl-17α, 21-(1'-methoxy-1'-pentyl-methylenedioxy)-pregna-1,4-diene-3,20-dione) (m.p. 148°-151° C) in 2.5 ml of DMF, 0.06 ml of phosphorus oxychloride was added. After keeping at room temperature for 40 min., the reaction temperature was evaporated in vacuo to give the crude solid. By recrystallization from acetone-ether, the pure product, m.p. 175°-177° C., was obtained in 39 mg yield.

EXAMPLE 156

Preparation of betamethasone 17-cyclopentanecarboxylate 21-chloride (17α-cyclopentancarbonyloxy-21-chloro-9α-fluoro-11β-hydroxy-16β-methyl-pregna-1,4-dien-3,20-dione)

To a solution of 50 mg of betamethasone 17,21-methyl orthocyclpentanecarboxylate (9α-fluoro-11β-hydroxy-16β-methyl-17α,21-(1'-cyclopentyl-1'-methoxy-methylenedioxy)-pregna-1,4-dien-3,20-dione) (m.p. 163°-167° C) in 5 ml of DMF, 0.06 ml of phosphorus oxychloride was added. After keeping at room temperature for 45 min., the mixture was evaporated in vacuo to give the crude solid. Recrystallization from acetone-ether afforded 38 mg of the pure product, m.p. 229°-231° C.

EXAMPLE 157

Preparation of betamethasone 17-benzoate 21-chloride(17α-benzoyloxy-21-chloro-9α-fluoro-11β-hydroxy-16β-methyl-pregna-1,4-dien-3,20-dione)

To a mixture of 100 mg of betamethasone 17,21-methyl orthobenzoate (9α-fluoro-11β-hydroxy-16β-methyl-17α,21-(1'-methoxy-1'-phenyl-methylenedioxy)-pregna-1,4-dien-3,20-dione) (m.p. 160°-172° C) in 6 ml of DMF, 0.12 ml of phosphorus oxychloride was added. The reaction mixture was allowed to stand at room temperature for 60 min., and then was evaporated in vacuo, to give the crude product. The pure one, m.p. 233°-237° C. was obtained by recrystallization from acetone-hexane-isopropylether in 82 mg yield.

EXAMPLE 158

In the procedure of Example 136, when phenylphosphoryl dichloride ($C_6H_5OPOCl_2$) was used as a reagent instead of phosphorus oxychloride, the pure product, m.p. 224°-227° C, was obtained in the 80 mg yield.

EXAMPLE 159

In the procedure of Example 136, when diphenylphosphoryl chloride $((C_6H_5O)_2POCl)$ was used instead of phosphorus oxychloride as a reagent, the pure product, m.p. 223°-226° C, was obtained in 80 mg yield.

EXAMPLE 160

In the procedure of Example 136, when methylphenoxyphosphinic chloride $((CH_3)(C_6H_5O)POCl)$ was used as a reagent instead of phosphorus oxychloride 82 mg of pure compound (m.p. 223°-227° C) was obtained.

EXAMPLE 161

In the procedure of Example 136, when methylphenylphosphoryl chloride $((CH_3O)(C_6H_5O)POCl)$ was used instead of phosphorus oxychloride as a reagent, 81 mg of pure product, m.p. 224°–227° C, was obtained.

EXAMPLE 162

In the procedure of Example 136, when ethylphosphoryl dichloride $(C_2H_5OPOCl_2)$ was used instead of phosphorus oxychloride as a reagent, the pure product was obtained in the 80 mg yield.

EXAMPLE 163

In the procedure of Example 137, when diethylphosphoryl chloride $((C_2H_5O)_2POCl)$ was used as a reagent instead of phosphorus oxychloride, the pure product was obtained in the 85 mg yield.

EXAMPLE 164

In the procedure of Example 137, when methylphenylphosphinic chloride $((CH_3)(C_6H_5)POCl)$ was used instead of phosphorus oxychloride as a reagent, the pure product was obtained in the 83 mg yield.

EXAMPLE 165

In the procedure of Example 137, when diethylphosphinic chloride $((C_2H_5)_2POCl)$ was used as a reagent instead of phosphorus oxychloride, the pure product, m.p. 192°–196° C, was obtained in the 82 mg yield.

EXAMPLE 166

In the procedure of Example 137, when ethylphosphinic dichloride $(C_2H_5POCl_2)$ was used as a reagent instead of phosphorus oxychloride, the pure product was obtained in the 82 mg yield.

EXAMPLE 167

In the procedure of Example 137, when phenylphosphoryl dichloride $(C_6H_5OPOCl_2)$ was used as a reagent instead of phosphorus oxychloride, the pure product was obtained in the 80 mg yield.

EXAMPLE 168

In the procedure of Example 137, when diphenylphosphoryl oxychloride $((C_6H_5O)_2POCl)$ was used as a reagent instead of phosphorus oxychloride, 82 mg of pure compound, m.p. 192°–196° C, was obtained.

EXAMPLE 169

In the procedure of Example 137, when diethylphosphoryl chloride $((C_2H_5O)_2POCl)$ was used as a reagent instead of phosphorus oxychloride, the pure product was obtained in the 84 mg yield.

EXAMPLE 170

In the procedure of Example 138, when diethylphosphinic chloride $((C_2H_5)_2POCl)$ was used instead of phosphorus oxychloride as a reagent, 85 mg of the pure compound, m.p. 154°–156° C, was obtained in the 85 mg yield.

EXAMPLE 171

In the procedure of Example 140, when diphenylphosphoryl chloride $((C_6H_5O)_2POCl)$ was used as a reagent instead of phosphorus oxychloride, the pure product, m.p. 226°–228° C, was obtained in the 79 mg yield.

EXAMPLE 172

In the procedure of Example 140, when methylphenylphosphinic chloride was used as a reagent instead of phosphorus oxychloride, the pure product was obtained in the 77 mg yield.

EXAMPLE 173

In the procedure of Example 142, when phenylphosphoryl dichloride $(C_6H_5OPOCl_2)$ was used instead of phosphorus oxychloride as a reagent, the pure product, m.p. 225°–227° C, was obtained in the 82 mg yield.

EXAMPLE 174

In the procedure of Example 143, when diphenylphosphoryl chloraide was used as a reagent instead of phosphorus oxychloride, the pure product was obtained in the 82 mg yield.

EXAMPLE 175

In the procedure of Example 147, when diethylphosphinic chloride $((C_2H_5)_2POCl)$ was used as a reagent instead of phosphorus oxychloride, the pure product, m.p. 230–232° C (dec.) was obtained in the 77 mg yield.

EXAMPLE 176

In the procedure of Example 148, when phenylphosphoryl dichloride $(C_6H_5OPOCl_2)$ was used as a reagent instead of phorphorus oxychloride, 83 mg of the pure product was obtained.

EXAMPLE 177

In the procedure of Example 150, when ethylphosphoryl dichloride $(C_2H_5OPOCl_2)$ was used as a reagent instead of phosphorus oxychloride, the pure product, m.p. 193–196° C, was obtained in the 87 mg yield.

EXAMPLE 178

In the procedure of Example 151, when ethylphosphinic dichloride was used instead of phosphorus oxychloride as a reagent, 45 mg of the pure product was obtained.

EXAMPLE 179

In the procedure of Example 152, when diphenylphosphoryl chloride $((C_6H_5O)_2POCl)$ was used as a reagent instead of phosphorus oxychloride, 34 mg of the pure product was obtained.

EXAMPLE 180

In the procedure of Example 155, when ethylphosphinic dichloride $(C_2H_5POCl_2)$ was used as a reagent instead of phosphorus oxychloride, 33 mg of the pure product was obtained.

EXAMPLE 181

In the procedure of Example 156, when phenylphosphoryl dichloride $(C_6H_5OPOCl_2)$ was used as a reagent instead of phosphorus oxychloride, the pure product, m.p. 229°–231° C, was obtained in the 34 mg yield.

EXAMPLE 182

(a) In the procedure of Example 157, when diphenylphosphoryl chloride was used as a reagent instead of phosphorus oxychloride, the pure compound, m.p. 233°–236° C, was obtained in the 79 mg yield.

(b) In the procedure of Example 157, when phenylphosphoryl dichloride was used as a reagent instead of phosphorus oxychloride, 42 mg of the pure product was obtained.

EXAMPLE 183

Preparation of hydrocortisone 17-propionate 21-bromide (21-bromo-11β-hydroxy-17α-propionyoxy-4-pregnen-3,20-dione)

To a solution of 100 mg off hydrocortisone 17,21-ethyl orthopropionate (17α,21-(1'-ethyl-1'-ethoxymethylenedioxy)-11β-hydroxy-4-pregnen-3,20-dione) (m.p. 182.5°-183.5° C) in 6 ml of DMF, 0.12 ml of phosphorus oxybromide was added. After keeping at room temperature for 30 min., the reaction mixture was evaporated in vacuo to give the crude product. Recrystallization from acetone of this provided the pure product, m.p. 185°-189° C in the 85 mg yield.

EXAMPLE 184

Preparation of hydrocortisone 17-butyrate 21-bromide (21-bromo-17α-butyryloxy-11β-hydroxy-4-pregnen-3,20-dione)

To a solution of 100 mg of hydrocortisone 17,21-methyl orthobutyrate (17α,21-(1'-methoxy-1'-propylmethylenedioxy)-11β-hydroxy-4-pregnen-3,20-dione) (m.p. 185.5-187.5° C) in 6 ml of DMF-dimethylsulfoxide (1:1), 0.12 ml of phosphorus oxybromide was added. The mixture was allowed to stand at room temperature for 35 min., and then was evaporated in vacuo to give the crude product. The pure one, m.p. 193°-194° C, was obtained by recrystallization from acetone-hexane in the 87 mg yield.

EXAMPLE 185

Preparation of betamethasone 17-acetate 21-bromide (17α-acetoxy-21-bromo-9α-fluoro-11β-hydroxy-16β-methyl-pregna-1,4-dien-3,20-dione)

To a solution of 50 mg of betamethasone 17,21-methyl orthoacetate (m.p. 156°-157° C) in 3 ml of DMF, 0.06 ml of phosphorus oxybromide was added. After keeping at room temperature for 30 min., the mixture was poured into ice-water and was extracted with chloroform. The extract was washed with aq. sodium bicarbonate solution, and water, dried over Na₂SO₄, and evaporated in vacuo to give the crude product. The pure product (m.p. 209°-212° C) was obtained by recrystallization from ethyl acetate-hexane in the 45 mg yield.

EXAMPLE 186

Preparation of betamethasone 17-propionate 21-bromide (21-bromo-9α-fluoro-11β-hydroxy-16β-methyl-17α-propionyloxy-pregna-1,4-dien-3,20-dione)

A mixture prepared from 50 mg of betamethasone 17,21-ethyl orthopropionate (m.p. 208°-211° C), 3.0 ml of DMF and 0.06 ml of phosphorus oxybromide was allowed to stand at room temperature for 40 min. Then, treatment of the mixture by the similar method as described in Example 185 provided the crude product. The pure product (m.p. 203°-205° C) was obtained by recrystallization from acetonehexane in the 41 mg yield.

EXAMPLE 187

Preparation of betamethasone 17-butyrate 21-bromide (21-bromo-17α-butyryloxy-9α-fluoro-16β-methyl-11β-hydroxy-pregna-1,4-dien-3,20-dione)

When a solution of 50 mg of betamethasone 17,21-methyl orthobutyrate (m.p. 148° C) dissolved in 3 ml of DMF was treated 0.08 ml of phosphorus oxybromide by the similar method as described in Example 185, the crude product was obtained. Recrystallization of this from ethyl acetate-hexane gave 43 mg of the pure product, m.p. 183°-185° C.

EXAMPLE 188

Preparation of dexamethasone 17-propionate 21-bromide (21-bromo-9α-fluoro-11β-hydroxy-16α-methyl-17α-propionyloxy-pregna-1,4-dien-3,20-dione)

A mixture prepared from 50 mg of dexamethasone 17,21-ethyl orthopropionate (m.p. 180°-184° C), 3.0 ml of DMF and 0.08 ml of phosphorus oxybromide was treated by the similar method as described in Example 185. A 44 mg of pure product (m.p. 224°-226° C(dec.)) was obtained by recrystallization of the crude product from acetone-hexane.

EXAMPLE 189

Preparation of dexamethasone 17-butyrate 21-bromide (21-bromo-17α-butyryloxy-9α-fluoro-11β-hydroxy-16α-methyl-pregna-1,4-dien-3,20-dione)

(a) A mixture prepared from 50 mg of dexamethasone 17,21-methyl orthobutyrate (m.p. 166°-169° C), 3 ml of DMF and 0.08 ml of phosphorus oxybromide was treated by the similar method as described in Example 188. A 41 mg of pure product (m.p. 221°-224° C) was obtained by recrystallization of the crude product from acetone-hexane.

(b) In the procedure (a), 25 mg of the starting material was converted to the 19 mg of the pure product (m.p. 221°-224° C(dec.)) by using HMPA as a solvent instead of DMF.

EXAMPLE 190

Preparation of hydrocortisone 17-propionate 21-chloride (a) To a solution of 50 mg of hydrocortisone 17,21-ethyl orthopropionate (17α,21-(1'-ethyl-1'-ethoxymethylenedioxy)-11β-hydroxy-4-pregnen-3,20-dione) (m.p. 182.5°-183.5° C) in 5 ml of DMF, a solution of 0.12 mg of methanesulfonyl chloride in 2 ml of DMF was added. The reaction mixture was allowed to stand at room temperature for 25 min. Then, the mixture was poured into ice-water and extracted with dichloromethane. The extract was washed with dil. sodium bicarbonate soln. and water, and dried over sodium sulfate. Evaporation in vacuo gave a crude product. The pure product, m.p. 225°-227° C, was obtained by recrystallization of the crude one thus obtained from acetone in the 46 mg yield.

(b) In the procedure of (a), when 0.13 ml of ethanesulfonyl chloride was used as a reagent instead of methanesulfonyl chloride, the pure product was obtained in the 42 mg yield.

(c) In the procedure of (a), when 0.15 ml of benzenesulfonyl chloride was used as a reagent, 41 mg of the pure product was obtained.

(d) In the procedure of (a), when p-toluenesulfonyl chloride was used as a reagent, 44 mg of the pure product was obtained.

EXAMPLE 191

Preparation of hydrocortisone 17-butyrate 21-chloride (a) To a solution of 50 mg of hydrocortisone 17,21-methyl orthobutyrate (17α,21-(1'-methoxy-1'-propyl-methylenedioxy)-11β-hydroxy-4-pregnen-3,20-dione) (m.p. 185.5°–187.5° C) in 5 ml of DMF, a solution of 0.12 ml of methanesulfonyl chloride in 0.25 ml of DMF was added. The reaction mixture was allowed to stand at room temperature for 30 min., and treated by the similar method as described in Example 190 (a). The pure product (m.p. 192°–196° C) was obtained by recrystallization of the crude one thus obtained from acetone-hexane in the 45 mg yield.

(b) In the procedure(a), when ethanesulfonyl chloride was used as a reagent instead of methanesulfonyl chloride, the pure product was obtained in the 44 mg yield.

(c) In the procedure(a), when benzenesulfonyl chloride was used as a reagent, the pure product was obtained in the 39 mg yield.

(d) In the procedure(a), when ethanesulfonyl chloride was used as a reagent, 44 mg of the product was obtained.

(e) In the procedure(a), when p-toluenesulfonyl chloride was used as a reagent, the product was obtained in the 42 mg yield.

EXAMPLE 192

Preparation of hydrocortisone 17-valerate 21-chloride

To a solution of 50 mg of hydrocortisone 17,21-methyl orthovalerate (17,21-(1'-butyl-1'-methoxy-methylenedioxy)-11β-hydroxy-4-pregnen-3,20-dione)(m.p. 163°–165° C) in 8 ml of DMF-dimethylsulfoxide (1:1), 0.12 mg of methanesulfonyl chloride was added. The mixture was allowed to stand at room temperature for 35 min., and then treated by the similar method as described in Example 190 (a). The pure product, m.p. 154°–156° C, was obtained in the 42 mg yield by recrystallization from acetone-hexane-isopropylether.

EXAMPLE 193

Preparation of hydrocortisone 17-caproate 21-chloride

To a solution of 50 mg of hydrocortisone 17,21-methyl orthocaproate (17α,21-(1'-methoxy-1'-pentyl-methylenedioxy)-11β-hydroxy-4-pregnen-3,20-dione) (m.p. 119°–120° C) in 8 ml of DMF, 0.12 ml of ethanesulfonyl chloride was added. After keeping at room temperature for 40 min., the reaction mixture was treated by the similar method as described in Example 190 (a). The pure product, m.p. 163°–167° C, was obtained by recrystallization of the crude solid thus obtained from acetone-hexane-isopropylether in the 41 mg yield.

EXAMPLE 194

Preparation of hydrocortisone 17-cyclopentanecarboxylate 21-chloride

To a solution of 50 mg of hydrocortisone 17,21-methyl orthocyclopentanecarboxylate (17α,21-(1'-cyclopentyl-1'-methoxy-methylenedioxy)-11β-hydroxy-4-pregnen-3,20-dione) (m.p. 197°–201° C) in 8 ml of DMF, 0.12 ml of methanesulfonyl chloride was added. The reaction mixture was allowed to stand at room temperature for 40 min., and treated by the similar method as described in Example 190 (a). Recrystallization of the crude product thus obtained from acetone-hexane-isopropylether gave the pure product, m.p. 229°–233° C, in the 39 mg yield.

EXAMPLE 195

Preparation of hydrocortisone 17-benzoate 21-chloride

To a solution of 50 mg of hydrocortisone 17,21-methyl orthobenzoate (17α,21-(1'-methoxy-1'-phenyl-methylenedioxy)-11β-hydroxy-4-pregnen-3,20-dione) (m.p. 208°–210° C) in 6 ml of DMF, a mixture of 0.14 mg of methanesulfonyl chloride and 2 ml of DMF was added. The reaction mixture was treated by the similar method as described in Example 190 (a). The crude product thus obtained was recrystallized from acetone-hexane to give the pure product, m.p. 226°–227°, in the 37 mg yield.

EXAMPLE 196

Preparation of prednisolone 17-butyrate 21-chloride

By the similar procedure as described in Example 195 (a), 50 mg of prednisolone 17,21-methyl orthobutyrate (17α,21-(1'-methoxy-1'-propyl-methylenedioxy)-11β-hydroxy-pregna-1,4-dien-3,20-dione) (m.p. 165°–168° C) was converted to 41 mg of the desired compound, m.p. 197°–200° C.

EXAMPLE 197

Preparation of prednisolone 17-valerate 21-chloride

To a solution of 25 mg of prednisolone 17,21-methyl orthovalerate (17α,21-(1'-butyl-1'-methoxy-methylenedioxy)-11β-hydroxy-pregna-1,4-dien-3,20-dione) (m.p. 157°–159° C) in 2 ml of dimethylsulfoxide, a mixture of 0.08 ml of ethanesulfonyl chloride and 2 ml of DMF was added. The mixture was allowed to stand at room temperature for 30 min., and then preparative thin-layer chromatographic separation and recrystallization from acetone-hexane-isopropyl ether yielded 21 mg of the pure product, m.p. 191°–193° C.

EXAMPLE 198

Preparation of dexamethasone 17-butyrate 21-chloride (a) 50 mg of dexamethasone 17,21-methyl orthobutyrate (9α-fluoro-17β,21-(1'-methoxy-1'-propyl-methylenedioxy)-11β-hydroxy-16α-methyl-pregna-1,4-dien-3,20-dione) (m.p. 166°–169° C) was treated by the similar method as described in Example 190 (a). Recrystallization of the crude product thus obtained from acetone-hexane gave 41 mg of the pure product, m.p. 230°–232° C.

(b) In the procedure (a), when p-toluenesulfonyl chloride (0.14 mg) was used as a reagent, the pure product was obtained in the 38 mg yield.

EXAMPLE 199

Preparation of dexamethasone 17-valerate 21-chloride (a) 50 mg of dexamethasone 17,21-methyl orthovalerate (9α-fluoro-17α,21-(1'-butyl-1'-methoxy-methylenedioxy)-11β-hydroxy-16α-methyl-pregna-1,4-dien-3,20-dione) (m.p. 157°–161° C) was treated by the similar method as described in Example 190 (a). Recrystallization from acetone-hexane of the crude product thus obtained yielded 38 mg of the pure product, m.p. 193°–195° C.

(b) In the procedure (a), when benzenesulfonyl chloride (0.14 mg) was used as a reagent, the pure product was obtained in the 38 mg yield by using preparative thin-layer chromatography.

EXAMPLE 200

Preparation of betamethasone 17-propionate 21-chloride (a) Treatment of 50 mg of betamethasone 17,21-ethyl orthopropionate (9α-fluoro-17α,21-(1'-ethyl-1'-ethoxymethylenedioxy) 11β-hydroxy-16β-methyl-pregna-1,4-dien-3,20-dione) (m.p. 208°–211° C) with 0.12 mg of methanesulfonyl chloride provided the crude product by the similar method as described in Example 190 (a). The pure one, m.p. 193°–196° C, was obtained by recrystallization of the crude product in the 47 mg yield.

(b) In the procedure (a), when 0.13 mg of ethanesulfonyl chloride was used, 45 mg of the product, m.p. 193°–196° C, was obtained.

(c) In the procedure (a), when p-toluenesulfonyl chloride was used as a reagent, the pure product, m.p. 193°–196° C, was obtained in the 44 mg yield.

EXAMPLE 201

Preparation of betamethasone 17-butyrate 21-chloride

By the similar procedure as described in Example 190 (a), treatment of 50 mg of betamethasone 17,21-methyl orthobutyrate (9α-fluoro-11β-hydroxy-17α,21-(1'-methoxy-1'-propyl-methylenedioxy) - 16β - methyl-pregna-1,4-diene-3,20-dione) (m.p. 148° C) with 0.12 mg of methanesulfonyl chloride provided the crude product. Recrystallization of the product from acetone-hexane gave 43 mg of the pure product, m.p. 171°–173° C.

EXAMPLE 202

Preparation of betamethasone 17-isobutyrate 21-chloride

By the similar method as described in Example 190 (a), a solution of 50 mg of betamethasone 17,21-methyl orthoisobutyrate (9α-fluoro-11β-hydroxy-17α,21-(1'-isopropyl-1'-methoxy-methylenedioxy)-16β-methyl-pregna-1,4-dien-3,20-dione) (m.p. 173° C) in 8 ml of DMF was treated with 0.13 mg of ethanesulfonyl chloride. Recrystallization of the crude product thus obtained from acetone-hexane provided 42 mg of the title compound, m.p. 192°–194° C.

EXAMPLE 203

Preparation of betamethasone 17-valerate 21-chloride 50 mg of betamethasone 17,21-methyl orthovalerate (9α-fluoro-17α,21-(1'-butyl-1'-methoxy-methylenedioxy)-11β-hydroxy-16β-methyl pregna-1,4-dien-3,20-dione) (m.p. 152°–154° C) was converted into 40 mg of the title compound, m.p. 197°–201° C, by using 0.12 mg of methanesulfonyl chloride.

EXAMPLE 204

Preparation of betamethasone 17-benzoate 21-chloride 50 mg of betamethsone 17,21-methyl orthobenzoate (9α-fluoro-11β-hydroxy-17α,21-(1'-methoxy-1'-phenyl-methylenedioxy)-16β-methyl-pregna-1,4-dien-3,20-dione) (m.p. 169°–172° C) was treated with 0.12 mg of methanesulfonyl chloride by the similar method as described in Example 190 (a). The crude product thus obtained was recrystallized from acetone-hexane-isopropyl ether to give the pure product, m.p. 233°–237° C, in the 38 mg yield.

EXAMPLE 205

Preparation of hydrocortisone 17-propionate 21-bromide

To a solution of 50 mg of hydrocortisone 17,21-ethyl orthopropionate (17α,21-(1'-ethyl-1'-ethoxy-methylenedioxy)-11β-hydroxy-4-pregnen-3,20-dione) (m.p. 182.5°–183.5° C) in 5 ml of DMF, a solution of 0.12 mg of methanesulfonyl bromide in 3 ml of DMF was added. The reaction mixture was allowed to stand at room temperature for 30 min. The preparative thin layer chromatographic separation and recrystallization from acetone-hexane provided 38 mg of the product.

EXAMPLE 206

Preparation of hydrocortisone 17-butyrate 21-bromide (a) To a solution of 50 mg of hydrocortisone 17,21-methyl orthobutyrate (17α,21-(1'-methoxy-1'-propyl-methylenedioxy)-11β-hydroxy-4-pregnen-3,20-dione) (m.p. 185.5°–187.5° C) in 5 ml of DMF, 0.12 mg of methanesulfonyl bromide in 3 ml of DMF was added. After keeping at room temperature for 30 min., the reaction mixture was poured into ice-water, and was extracted with chloroform. The extract was washed with dil. sodium bicarbonate solution and water, dried over sodium sulfate, and evaporated in vacuo to give a crude product. Pure product, m.p. 193°–194° C, was obtained by recrystallization from acetone-hexane in the 41 mg yield.

(b) In the procedure (a), when p-toluenesulfonyl bromide was used as a reagent instead of methanesulfonyl bromide, 34 mg of the pure product was obtained.

EXAMPLE 207

Preparation of betamethasone 17-propionate 21-bromide

According to the method as described in Example 205, treatment of 50 mg of betamethasone 17,21-ethyl orthopropionate (m.p. 208°–211° C) with 0.12 mg of methanesulfonyl bromide provided the title compound, m.p. 203°–205° C, in the 45 mg yield.

EXAMPLE 208

Preparation of betamethasone 17-butyrate 21-bromide

A mixture prepared from 25 mg of betamethasone 17,21-methyl orthobutyrate (m.p. 148° C), 5 ml of DMF and 0.08 mg of methanesulfonyl bromide was kept at room temperature for 35 min. The mixture was poured into ice-water and extracted with methylene chloride. The extract was treated by the similar method as described in Example 206 to give the crude product. Pure one, m.p. 183°–185° C, was obtained by recrystallization from ethyl acetate-hexane in the 20 mg yield.

EXAMPLE 209

In the procedure as described in Example 191 (a), when chlorosulfonic acid was used as a reagent, the pure product was obtained in the 42 mg yield.

EXAMPLE 210

In the procedure as described in Example 200, when chlorosulfonic acid was used as a reagent, 45 mg of the pure product (m.p. 193°–196° C) was obtained.

EXAMPLE 211

In the procedure as described in Example 203, when chlorosulfonic acid was used as a reagent, the pure product, (m.p. 197°–201° C) was obtained in the 38 mg yield.

EXAMPLE 212

Preparation of hydrocortisone 17-acetate 21-chloride (a) To a solution of hydrocortisone 17,21-methyl orthoacetate [17α,21-(1'-methyl-1'-methoxy-methylenedioxy)-4-pregen-11β-hydroxy-3,20-dione](50 mg, m.p. 222°–224° C) dissolved in dimethyl sulfoxide (abbreviate DMF below) (5 ml), N-chlorosuccinimide (15 mg) was added. The reaction mixture was allowed to stand at room temperature for 60 min. Then the reaction mixture was poured into ice-water and extracted with chloroform. The extract was washed with dil. sodium thiosulfate soln., then thoroughly with water, dried over sodium sulfate and concentrated in vacuo to give the crude product, which was recrystallized from acetone-hexane-isopropylether. Yield, 45 mg, m.p. 253°–254° C.

(b) The reaction described in (a) was repeated. Then, after adsorption on silica gel thin-layer chromatoplate directly, the reaction mixture was subjected to preparative thin-layer chromatography. The crude product thus obtained was recrystallized from the same solvent as described in (a) to give 46 mg of the pure sample (m.p. 252°–254° C)

EXAMPLE 213

Preparation of hydrocortisone 17-butyrate 21-chloride

To a solution of hydrocortisone 17,21-methyl orthobutyrate [17α,21 -(1'-methoxy-1'-propyl-methylenedioxy)-11β-hydroxy-4-pregnen-3,20-dione] (50 mg) (m.p. 185.8°–187.5° C) dissolved in DMF (5 ml), N-chlorosuccinimide (15 mg) was added. The reaction mixture was treated by the similar method as described in Example 212 (a) to give the crude product, which was recrystallized from acetone-hexane. Yield 45 mg, m.p. 192°–196° C.

EXAMPLE 214

Preparation of hydrocortisone 17-valerate 21-chloride

To a solution of hydrocortisone 17,21-methyl orthovalerate [17α,21-(1'-butyl-1'-methoxy-methylenedioxy)-11β-hydroxy-4-pregnen-3,20-dione] (50 mg, m.p. 163°–165° C) dissolved in DMF (5 ml), methylene chloride soln. containing N-chlorosuccinimide (15 mg) was added. The reaction mixture was allowed to stand at room temperature for 90 min., poured into ice-water and extracted with methylene chloride. The extract was washed with dil. sodium thiosulfate soln., then thoroughly with water, dried over sodium sulfate and concentrated in vacuo to give the residue, which was recrystallized from -acetone-hexane-isopropylether. Yield 42 mg, m.p. 154°–156° C.

EXAMPLE 215

Preparation of hydrocortisone 17-benzoate 21-chloride

To a solution of hydrocortisone 17,21-methyl orthobenzoate [17α,21-(1'-methoxy-1'-phenyl-methylenedioxy)-11β-hydroxy-4-pregnen-3,20-dione] (25 mg, m.p. 209°–210° C) dissolved in DMF (6 ml), N-chlorosuccinimide (8 mg) was added. The reaction mixture was allowed to stand at room temperature for 90 min., and treated by the similar method as described in Example 212. The crude product thus obtained was recrystallized from acetone-hexane to give 37 mg of the pure product, m.p. 226°–229° C.

EXAMPLE 216

Preparation of betamethasone 17-propionate 21-chloride

To a solution of betamethasone 17,21-ethyl orthopropionate [9α-fluoro-16β-methyl-17α,21-(1'-ethyl-1'-ethoxy-methylenedioxy)-11β-hydroxy-pregna-1,4-dien-3,20-dione] (50 mg, m.p. 208°–211° C) dissolved in DMF (5 ml), N-chlorosuccinimide (15 mg) was added. Then, the reaction mixture was treated by the similar procedure as described in Example 212 (a). The crude product thus obtained was recrystallized from acetone-hexane to give 47 mg of the pure product (m.p. 193°–196° C).

EXAMPLE 217

Preparation of betamethasone 17-butyrate 21-chloride

To a solution of betamethasone 17,21-methyl orthobutyrate [9α-fluoro-16β-methyl-11β-hydroxy-17α,21-(1'-methoxy-1'-propyl-methylenedioxy)-pregna-1,4-dien-3,20-dione] (50 mg, m.p. 148° C) dissolved in DMF (5 ml), N-chlorosuccinimide (15 mg) was added. Then, the reaction mixture was treated by the similar procedure as described in Example 212 (a). The crude product thus obtained was recrystallized from acetone-hexane to give 42 mg of the pure product (m.p. 171°–173° C).

EXAMPLE 218

Preparation of betamethasone 17-valerate 21-chloride

To a solution of betamethasone 17,21-methyl orthovalerate [9α-fluoro-16β-methyl-17α,21-(1'-butyl-1'-methoxy-methylenedioxy)-11β-hydroxy-pregna-1,4-dien-3,20-dione] (25 mg, m.p. 152°–154° C) dissolved in DMF-dimethyl sulfoxide (1:1) (3 ml), N-chlorosuccinimide (8 mg) was added. The reaction mixture was allowed to stand at room temperature and treated by the similar method as described in Example 212 (a). The crude product thus obtained was recrystallized from acetone-hexane-isopropylether to give 20 mg of the pure product (m.p. 197°–201° C).

EXAMPLE 219

Preparation of betamethasone 17-cyclopentanecarboxylate 21-chloride

To a solution of betamethasone 17,21-methyl orthocyclopentanecarboxylate [9α-fluoro-16β-methyl-11β-hydroxy-17α,21-(1'-methoxy-1'-cyclopentyl-methylenedioxy)-pregna-1,4-dien-3,20-dione] (50 mg, m.p. 169°–172° C) dissolved in DMF (6 ml), N-chlorosuccinimide (18 mg) was added. The reaction mixture was allowed to stand at room temperature for 90 min., and treated by the similar method as described in Example 212 (b). The crude product thus obtained was recrystallized from acetone-hexane-isopropylether to give 37 mg of the pure product (m.p. 229°–231° C).

EXAMPLE 220

Preparation of betamethasone 17-benzoate 21-chloride

To a solution of betamethasone 17,21-methyl orthobenzoate [9α-fluoro-11β-hydroxy-16β-methyl-17α-

21-(1'-methoxy-1'-phenyl-methylenedioxy)-pregna-1,4-dien-3,20-dione] (50 mg, m.p. 169°–172° C) dissolved in DMF (6 ml), N-chlorosuccinimide (18 mg) was added. The reaction mixture was allowed to stand at room temperature and treated by the similar method as described in Example 212 (a). The crude product thus obtained was recrystallized from acetone-hexane-isopropyl ether to give 35 mg of the pure product (m.p. 233°–237° C).

EXAMPLE 221

Preparation of hydrocortisone 17-propionate 21-bromide (a) To a solution of hydrocortisone 17,21-ethyl orthopropionate [17α,21-(1'-ethyl-1'-ethoxy-methylenedioxy)-11β-hydroxy-4-pregnen-3,20-dione] (mp. 182°–183.5° C) (50 mg) dissolved in DMF (6 ml), N-bromosuccinimide (15 mg) was added. The reaction mixture was allowed to stand at room temperature for 65 min. and treated by the similar method as described in Example 212 (a). The crude product thus obtained was recrystallized from acetone-hexane to give 45 mg of the pure product (m.p. 185°–189° C).

(b) An analogous experiment of (a) by using N-bromo-phthalimide as a reagent provided 38 mg of the pure product (m.p. 185°–188° C) after the similar treatment.

EXAMPLE 222

Preparation of hydrocortisone 17-butyrate 21-bromide (a) To a solution of 50 mg of hydrocortisone 17,21-methyl orthobutyrate [17α,21-(1'-methoxy-1'-propyl-methylenedioxy)-11β-hydroxy-4-pregnen-3,20-dione] (m.p. 185°–187.5° C) dissolved in DMF (6 ml), N-bromosuccinimide (15 mg) was added. The reaction mixture was allowed to stand at room temperature for 70 min. and treated by the similar method as described in Example 212 (a). The crude product thus obtained was recrystallized from acetone-hexane to give 43 mg of the pure product (m.p. 193°–194° C).

An analogous experiment of above (a) by using N-bromoacetamide as a reagent was repeated. The reaction mixture was submitted to the preparative thin-layer chromatography as indicated in Example 212 (b). Similar recrystallization as (a) of the crude product thus obtained provided 38 mg of the pure product (m.p. 193°–194° C).

(c) An analogous experiment of above (a) with N-bromophthalimide as a reagent was repeated. The reaction mixture was submitted to the preparative thin-layer chromatography as indicated in Example 212 (b). Similar recrystallization as (a) of the crude product thus obtained provided 31 mg of the pure product (m.p. 193°–194° C).

EXAMPLE 223

Preparation of dexamethasone 17-propionate 21-bromide

A mixture prepared from dexamethasone 17,21-ethyl orthopropionate (m.p. 180°–184° C) (50 mg), DMF (6 ml) and N-bromosuccinimide (15 mg) was allowed to stand at room temperature for 70 min. The reaction mixture was treated by the similar method as described in Example 212 (a) to give the crude product. Recrystallization of this from acetone-hexane provided 47 mg of the pure product (m.p. 224°–226° C (dec.)).

EXAMPLE 224

Preparation of betamethasone 17-propionate 21-bromide

To a solution of 50 mg of betamethasone 17,21-ethyl orthopropionate (m.p. 208°–211° C) in 6 ml of DMF, 16 mg of N-bromosuccinimide was added. After similar treatment as described in Example 212 (a), the crude product was obtained. Similar recrystallization provided 45 mg of the pure product (m.p. 203°–205° C).

EXAMPLE 225

Preparation of betamethasone 17-butyrate 21-bromide (a) To a solution of 50 mg of betamethasone 17,21-methyl orthobutyrate (m.p. 148° C) dissolved in 6 ml of DMF, 16 mg of N-bromosuccinimide was added. After similar treatment as described in Example 212(a), the crude product was obtained. Recrystallization of this from ethyl acetate-hexane gave 41 mg of the pure product (m.p. 183°–185° C).

(b) An analogous experiment of above (a) was repeated by using N-bromoacetamide as a reagent. Separation of the substance from the reaction mixture was used the preparative thin-layer chromatographic technique as described in Example 212 (b). The crude product was recrystallized from ethyl acetate-hexane to give 35 mg of the pure product (m.p. 183°–185° C).

EXAMPLE 226

Preparation of betamethasone 17-propionate 21-iodide

To a solution of 50 mg of betamethasone 17,21-ethyl orthopropionate (m.p. 208°–211° C) dissolved in 6 ml of DMF, 16 mg of N-iodosuccinimide was added and the reaction mixture was allowed to stand at room temperature for 60 min. The preparative thin-layer chromatography of the reaction mixture provided the crude product, which was recrystallized from ethyl acetate-hexane to give 45 mg of the pure product (m.p. 167°–169° C (dec.)).

EXAMPLE 227

Preparation of betamethasone 17-butyrate 21-iodide

A mixture prepared from betamethasone 17,21-methyl orthobutyrate (m.p. 148° C) (50 mg), DMF (6 ml) and N-iodosuccinimide (16 mg) was allowed to stand at room temperature for 70 min. Similar treatment and recrystallization as described in Example 212(a) provided 41 mg of the crude product (m.p. 161°–163° C).

EXAMPLE 228

Preparation of hydrocortisone 17-propionate 21-chloride

To a solution of 100 mg of hydrocortisone 17,21-ethyl orthopropionate [17α,21-(1'-ethyl-1'-ethoxy-methylenedioxy)-11β-hydroxy-4-pregnen-3,20-dione](m.p. 182.5°–183.5° C) in 10 ml of DMF, a solution of 0.12 mg of phosphrous pentachloride was added. After being kept at room temperature for 13 min., the mixture was poured into ice-water. Then, this was extracted with dichloromethane. The extract was washed with dil. sodium bicarbonate soln. and water, and dried over sodium sulfate. Evaporation in vacuo gave a crude product. The pure product (m.p. 225°–227° C) was obtained by recrystallization of the crude one thus obtained from acetone-hexane in the 45 mg yield.

EXAMPLE 229

Preparation of hydrocortisone 17-butyrate 21-chloride

To a solution of 100 mg of hydrocortisone 17,21-methyl orthobutyrate [17α,21-(1'-methoxy-1'-propyl-methylenedioxy)-11β-hydroxy-4-pregnen-3,20-dione](m.p. 192°–196° C) in 5 ml of DMF, 30 mg of phosphorus pentachloride was added. The reaction mixture was allowed to stand at room temperature for 15 min., and treated by the similar method as described in Example 228. The pure product (m.p. 192°–196° C) was obtained by recrystallization of the crude one from acetone-hexane in the 94 mg yield.

EXAMPLE 230 preparation of hydrocortisone 17-valerate 21-chloride

To a solution of 50 mg of hydrocortisone 17,21-methyl orthovalerate [17α,21-(1'-butyl-1'-methoxymethylenedioxy)-11β-hydroxy-4-pregnen-3,20-dione](m.p. 163–165° C) in 2.5 ml of DMF, 15 mg of phosphorus pentachloride was added. The reaction mixture was allowed to stand at room temperature for 15 min. and treated by the similar method as described in Example 228. The pure product (m.p. 154°–156° C) was obtained by recrystallization of the crude one from acetone-hexane-isopropyl ether in the 41 mg yield.

EXAMPLE 231

Preparation of hydrocortisone 17-benzoate 21-chloride

To a solution of 50 mg of hydrocortisone 17,21-methyl orthobenzoate [17α,21-(1'-methoxy-1'-phenyl-methylenedioxy)-11β-hydroxy-4-pregnen-3,20-dione](m.p. 208°–210° C) in 6 ml of DMF, 15 mg of phosphorus pentachloride was added. After being kept at room temperature for 20 min., the reaction mixture was treated by the similar method as described in Example 228. The pure product (m.p. 225°–227° C) was obtained by recrystallization of the crude one from acetone-hexane in the 38 mg yield.

EXAMPLE 232

Preparation of betamethasone 17-propionate 21-chloride

To a solution of 100 mg of betamethasone 17,21-ethyl orthopropionate [9α-fluoro-16β-methyl-11β-hydroxy-17,21-(1'-ethyl-1'-ethoxy-methylenedioxy)-pregna-1,4-diene-3,20-dione](m.p. 208°–211° C) in 10 ml of DMF, 30 mg of phosphorus pentachloride was added. After being kept at room temperature for 12 min., the reaction mixture was treated by the similar method as described in Example 228. The pure product (m.p. 193°–196° C) was obtained by recrystallization from acetone-hexane in the 95 mg yield.

EXAMPLE 233

Preparation of bentamethasone 17-butyrate 21-chloride

To a solution of 50 mg of betamethasone 17,21-methyl orthobutyrate [9α-fluoro-11β-hydroxy-16β-methyl-17α,21-(1'-methoxy-1'-propyl-methylenedioxy)-pregna-1,4-diene-3,20-dione](m.p.148° C) in 5ml of DMF-DMSO (1:1), 15 mg of phosphorus pentachloride was added. The mixture was allowed to stand at room temperature for 16 min., and treated by the similar method as described in Example 228. The pure product, m.p. 171°–173° C, was obtained by recrystallization of the crude one from actone-hexane in the 44 mg yield.

EXAMPLE 234

Preparation of bentamethasone 17-valerate 21-chloride

By the similar method as described in Example 228, 26 mg of betamethasone 17,21-methyl orthovalerate (m.p.152°–154° C) was converted into the title compound, m.p. 197°–201° C, in the 22 mg yield.

EXAMPLE 235

Preparation of bentamethasone 17-benzoate 21-chloride

By the similar method as described in Example 228, treatment of 50 mg of betamethasone 17,21-methyl orthobenzoate [9α-fluoro-11β-hydroxy-16β-methyl-17β,21-(1'-methoxy-1'-phenyl-methylenedioxy)-pregna-1,4-diene-3,20-dione](m.p. 169°–172° C) with phosphorus pentachloride provided 35 mg of the title product, m.p. 233°–237° C.

EXAMPLE 236

Preparation of hydrocortisone 17-propionate 21-bromide

To a solution of 100 mg of hydrocortisone 17,21-ethyl orthiopropionate (17α,21-(1'-ethyl-1-ethoxy-methylenedioxy)-11β-hydroxy-4-pregnen-3,20-dione) (m.p. 182.5°–183.5° C) in 10 ml of DMF, 30 mg of phsophorus pentabromide was added. After keeping at room temperature for 14 min., the reaction mixture was poured into ice-water and extracted with methylene chloride. The extract was washed with dil. sodium bicarbonate solution and water, dried over sodium sulfate and evaporated in Vacuo to give the crude solid. The pure product, m.p. 185°–189° C, was obtained by recrystallization from acetone-hexane in the 85 mg yield.

EXAMPLE 237

Preparation of hydrocortisone 17-butyrate 21-bromide

A mixture of 50 mg of hydrocortisone 17,21-methyl orthobutyrate (17α,21-(1'-methoxy-1'-propyl-methylenedioxy)-11β-hydroxy-4-pregnen-3,20-dione) (m.p. 185.5°–187.5° C), 5ml of DMF and 15 mg of phosphorus pentabromide was treated by the similar method as described in Example 236 to give the crude product. The pure one, m.p. 193°–194° C, was obtained by recrystallization from acetone-hexane in the 42 mg yield.

EXAMPLE 238

Preparation of betamethasone 17-propionate 21-bromide

To a solution of 50 mg of betamethasone 17,21-ethyl orthopropionate (m.p. 208°–211° C) in 5 ml of DMF, 15 mg of phosphorus pentabromide was added. After keeping at room temperature for 12 min., the mixture was treated by the similar method as described in Example 236 to give the crude product. Recrystallization from acetone-hexane afforded 41 mg of the pure product, m.p. 203°–205° C.

EXAMPLE 239

Preparation of betamethasone 17-butyrate 21-bromide

A solution of 25 mg of betamethasone 17,21-methyl orthobutyrate (m.p. 148° C) in 2.5 mg of DMF-DMSO(1:1) was treated with phosphorus pentabromide for 18 min. at room temperature. Preparative thin-layer chromatographic separation and recrystallization from ethyl acetate-hexane provided 21 mg of the pure product, m.p. 183°–185° C.

EXAMPLE 240

Preparation of dexamethaxsone 17-butyrate 21-bromide

To a solution of 25 mg of dexamethasone 17,21-methyl orthobutyrate (m.p. 166°–169° C) in 2.5 ml of DMF, 18 mg of phosphorus pentabromide was added. The mixture was allowed to stand at room temperature for 25 min. and treated by the similar method as described in Example 236 to give the crude product. The pure one, m.p. 221°–224° C (dec.), was obtained by recrystallization from acetone-hexane in the 20 mg yield.

EXAMPLE 241

Preparation of betamethasone 17-propionate 21-fluoride

A mixture prepared from betamethasone 17,21-ethyl orthopropionate (m.p. 208°–211° C) (50 mg), DMF(4.5ml) and phosphorus pentafluoride (15 mg) was allowed to stand at room temperature for 30 min. Direct preparative thin-layer chromatography of the reaction mixture and recrystalization from acetone-hexane provided 37 mg of the pure product (m.p. 221°–224° C).

EXAMPLE 242

Preparaion of betamethasone 17-butyrate 21-fluoride

A mixture prepared from betamethasone 17,21-methyl orthobutyrate (m.p. 148° C) (50 mg), DMF (4.5 ml) and phosphorus pentafluoride(15mg) was treated by the similar method as described in Example 241 to give 33 mg of the pure product (m.p. 246°–248° C).

EXAMPLE 243

Preparation of dexamethasone 17-propionate 21-fluoride

A mixture prepared from dexamethasone 17,21-ethyl orthopropionate (m.p. 219°–221° C) (50 mg), DMF(4.5 ml) and phosphorus pentafluoride (15 mg) was treated by the similar method as described in Example 241. Recrystallization of the crude product thus obtained form acetone-hexane gave 35 mg of the pure product (m.p. 218°–222° C).

What we claim is:

1. A method for preparing a 17α-ester-21-halo pregnane of the formula

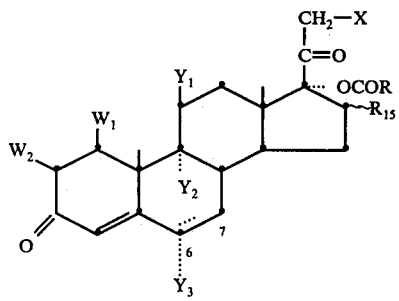

wherein R is selected from the group consisting of alkyl containing 1 to 9 carbon atoms, cycloalkyl containing 4 to 6 carbon atoms, phenyl, lower alkylphenyl, nitrophenyl and halophenyl, X is halogen, $Y_1$ is halogen, hydroxy or oxo, $Y_2$ is hydrogen or halogen, or $Y_1$ and $Y_2$, together with their adjacent carbon atoms, form an epoxy ring or a double bond, $Y_3$ is halogen, hydrogen or methyl, $W_1$ is hydrogen or methyl, $W_2$ is hydrogen or methyl, or $W_1$ and $W_2$, together with their adjacent carbon atoms, form a cyclopropane ring or a double bond, $R_{15}$ is hydrogen, methyl, methylene, hydroxy, lower alkoxy or acyloxy containing 2 to 8 carbon atoms, the wavy line ~ represents the α- or β- configuration, and the bond between the carbon atoms at the 6 and 7 positions is a single or double bond, which comprises reacting a 17α,21-cyclic orthoester of a 17α,21-dihydroxy pregnane of the formula

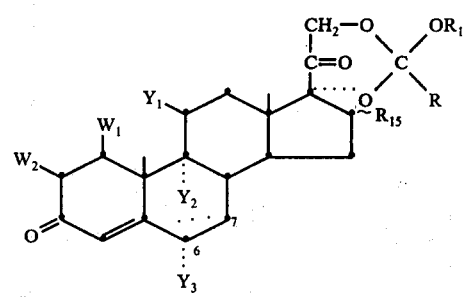

wherein Rhd 1 is lower alkyl and R, $Y_1$, $Y_2$, $Y_3$, $W_1$, $W_2$, $R_{15}$, the wavy line ~ and the bond between the carbon atoms at the 6 and 7 positions are as defined above, with a halo compound selected from the group consisting of silyl halides, acyl halides, phosphorus oxyhalides, sulfonyl halides, N-haloimides, N-haloamides and phosphorus pentahalides, in the presence of an organic polar solvent selected from the group consisting of dimethylformamide, N-methylpyrrolidone, hexamethylphosphoric triamide and dimethylsulfoxide, or a mixture of said organic polar solvent and an organic non-polar solvent, which mixture of solvents contains at least 50% by weight of the organic polar solvent.

2. A method according to claim 1, wherein the halo compound is a silyl halide of the formula

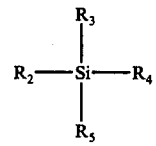

wherein one to three of $R_2$, $R_3$, $R_4$ and $R_5$ are halogen and the others are independently selected from the group consisting of lower alkyl, lower alkyl substituted by halogen, lower alkenyl, lower alkoxy and phenyl.

3. A method according to claim 1, wherein the halo compound is an acyl halide selected from the group consisting of compounds of the formulae

and
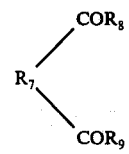

wherein $R_6$ is selected from the group consisting of (1) alkyl containing 1 to 18 carbon atoms, (2) said alkyl substituted by halogen, phenyl or phenoxy, (3) alkenyl containing 2 to 18 carbon atoms, (4) said alkenyl substituted by phenyl, (5) cycloalkyl containing 4 to 10 carbon atoms, (6) haloformyl, (7) lower alkoxycarbonyl, (8) aryl containing 6 to 12 carbon atoms and (9) unsaturated lactone rings containing 2 oxygen atoms and 4 to 7 carbon atoms, $R_7$ is selected from the group consisting of phenylene, vinylene and alkylene containing 1 to 10 carbon atoms, at least one of $R_8$ and $R_9$ is halogen and the other is lower alkoxy, and X is halogen.

4. A method according to claim 1, wherein the halo compound is a phosphorus oxyhalide of the formula

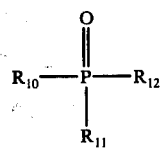

wherein one to three of $R_{10}$, $R_{11}$ and $R_{12}$ are halogen, and the others are independently selected from the group consisting of lower alkyl, lower alkoxy, phenyl and phenoxy.

5. A method according to claim 1, wherein the halo compound is a sulfonyl halide of the formula

wherein $R_{13}$ is selected from the group consisting of hydroxy, lower alkyl and phenyl, and X is halogen.

6. A method according to claim 1, wherein the halo compound is an N-halomide selected from the group consisting of N-halophthalimide and N-halosuccinimide.

7. A method according to claim 1, wherein the halo compound is an N-haloamide of the formula

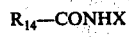

wherein $R_{14}$ is lower alkyl and X is halogen.

8. A method according to claim 1, wherein the halo compound is a phosphorus pentahalide of the formula

wherein X is halogen.

9. A method according to claim 1, wherein the 17 α-ester-21-halo pregnane is 17 α-ester-21-halo hydrocortisone, 17 α-ester-21-halo prednisolone, 17 α-ester-21-halo triamcinolone, 17 α-ester-21-halo dexamethasone, 17 α-ester-21-halo betamethasone, 17 α-ester-21-halo paramethasone or 17 α-ester-21-halo fluorocinolone.

10. A method according to claim 1, wherein the reaction temperature is within the range from room temperature to reflux temperature.

11. A method according to claim 10, wherein the reaction is carried out at room temperature for 0.5-3 hours.

12. A method according to claim 10, wherein the reaction is carried out a reflux temperature for 5-10 minutes.

13. A method according to claim 1, wherein the organic non-polar solvent is selected from the group consisting of benzene, cyclohexane, tetrahydrofurane, dioxane, ether, chloroform and ametylene chloride.

14. A method according to claim 1, wherein the halo compound is employed in a amount of 1 to 5 moles per mole of the 17 α,21-cyclic orthoester of a 17 α,21-dihydroxy pregnane.

15. A method according to claim 1, wherein the solvent or mixture of solvents is employed in an amount of 10 to 100 parts by weight per one part by weight of the 17 α,21-cyclic orthoester of a 17 α,21-dihydroxy pregnane.

* * * * *